(12) United States Patent
Krimmer et al.

(10) Patent No.: US 6,617,480 B2
(45) Date of Patent: *Sep. 9, 2003

(54) MOLECULAR WEIGHT-ENLARGED LIGANDS FOR ASYMMETRIC, HOMOGENEOUSLY SOLUBLE HYDROGENATION CATALYSTS, PROCESS FOR THE PRODUCTION THEREOF AND USE

(75) Inventors: Hans-Peter Krimmer, Dietzenbach (DE); Jens Woeltinger, Hanau (DE); Olaf Burkhardt, Kalmthout (BE); Ingo Klement, Pohlheim-Garbenteich (DE); Hans Henniges, Bonn (DE); Karlheinz Drauz, Freigericht (DE); Andreas Bommarius, Atlanta, GA (US); Jean-Louis Philippe, Dreieich (DE); Andreas Karau, Neustadt (DE)

(73) Assignee: Degussa AG, Duesseldorf (DE)

( * ) Notice: Subject to any disclaimer, the term of this patent is extended or adjusted under 35 U.S.C. 154(b) by 0 days.

This patent is subject to a terminal disclaimer.

(21) Appl. No.: 09/767,684

(22) Filed: Jan. 24, 2001

(65) Prior Publication Data

US 2002/0062004 A1 May 23, 2002

(30) Foreign Application Priority Data

Jan. 24, 2000 (DE) .......................... 100 02 976

(51) Int. Cl.$^7$ ............................ C07C 5/02; C08F 8/42; B01J 23/38
(52) U.S. Cl. .................. 585/275; 556/136; 556/137; 556/144; 525/326.1; 525/327.6; 525/329.8; 525/329.7; 525/340; 525/341; 525/360; 525/370; 502/155; 502/158; 502/159; 502/162; 502/167; 502/171; 502/313
(58) Field of Search ................. 556/136, 137, 556/144; 502/155, 158, 157, 162, 167, 171, 313; 525/326.1, 327.6, 327.8, 329.9, 340, 341, 360, 370; 585/275

(56) References Cited

U.S. PATENT DOCUMENTS

| | | | |
|---|---|---|---|
| 4,424,312 A | | 1/1984 | Stille |
| 4,605,750 A | | 8/1986 | Kumobayashi et al. |
| 4,634,775 A | | 1/1987 | Beck et al. |
| 4,695,631 A | | 9/1987 | Otsuka et al. |
| 5,043,474 A | * | 8/1991 | Muller et al. ............... 558/145 |
| 5,777,062 A | | 7/1998 | Pugin |
| 5,990,318 A | * | 11/1999 | Chan et al. ............... 528/272 |
| 6,087,481 A | | 7/2000 | Reetz et al. |
| 6,284,925 B1 | * | 9/2001 | Knochel et al. |
| 6,348,620 B1 | * | 2/2002 | Knochel et al. ........... 556/144 |
| 6,534,657 B2 | * | 3/2003 | Zhang ....................... 548/101 |

FOREIGN PATENT DOCUMENTS

| | | | |
|---|---|---|---|
| DE | 196 47 892 | | 6/1998 |
| DE | 197 30 657 A1 | | 6/1998 |
| DE | 199 21 924 | * | 12/1999 |
| DE | 199 56 374 | * | 6/2000 |
| EP | 0 592 881 | | 4/1994 |
| EP | 0 729 969 | | 9/1996 |
| EP | 0 877 029 | | 11/1998 |
| EP | 0 965 574 | * | 12/1999 |
| FR | 2 634 209 | | 1/1990 |
| JP | 2000-053593 | * | 2/2000 |
| JP | 2000-143684 | * | 5/2000 |
| WO | WO 98/12202 | | 3/1998 |
| WO | WO 98/22415 | | 5/1998 |
| WO | WO 99/62855 | | 12/1999 |

OTHER PUBLICATIONS

Dennis J. Gravert et al, "Soluble Supports Tailored for Organic Synthesis: Parallel Polymer Synthesis via Sequential Normal/Living Free Radical Processes", J. Am. Chem. Soc., 1998, 120, pp. 9481–9495.

Eberhard Steckhan et al, "Kontinuierliche Erzeugung von NADH aus NAD und Formiat mit einem molekulargewichtsvegoesserten Homogenkatalysator in einem Membranreaktor", Angew. Chem., 1990, 102, Nr. 4, pp. 445–447.

Manfred T. Reetz et al, "Synthease und katalytische Wirkung von dendritischen Diphosphan–Metallkomplexen", Angew. Chem., 1997, 109, Nr. 13/14, pp. 1559–1562.

Dieter Seebach et al, "Polymer–and Dendrimer–Bound Ti–TADDOLates in Catalytic (and Stoichiometric Enantioselective Reactions: Are Pentacoordinate Cationic Ti Complexes the Catalytically Active Species?", Helvetica Chimica Acta, 1996, vol. 79, pp. 1710–1740.

Udo Kragl et al, "Kontinuierliche asymmetrische Synthease in einem Membranreaktor", Angew. Chem., 1996, 108, Nr. 6, pp. 684–685.

Fritz Keller et al, "Chiral Polysiloxane–Fixed Metal 1,3–Diketonates (Chirasil–Metals) as Catalytic Lewis Acids for a Hetero Diels–Alder Reaction–Inversion of Enantioselectivity Upon Catalyst–Polymer Binding", Chem. Ber./Recueil, 1997, 130, pp. 879–885.

Carsten Bolm et al, "Asymmetrische Dihydroxylierung mit Polyethylenglycolmonomethylether–gebundenen Liganden", Angew. Chem. 1997, 109, Nr. 7, pp. 773–775.F (List continued on next page.)

Primary Examiner—Robert Dawson
Assistant Examiner—Jeffrey Robertson
(74) Attorney, Agent, or Firm—Oblon, Spivak, McClelland, Maier & Neustadt, P.C.

(57) ABSTRACT

The present invention relates to a molecular weight-enlarged, homogeneously soluble ligand, which includes:

an average molecular weight of at least 1000 g/mol;

a molecular weight-enlarging polymer;

optionally, a linker; and at least one homochiral active center;

wherein the active center is bound to the molecular weight-enlarging polymer through the linker or is bound directly to the molecular weight-enlarging polymer, methods of preparing, catalysts containing same, and methods of using same.

18 Claims, 1 Drawing Sheet

OTHER PUBLICATIONS

*Carsten Bolm et al*, "Polymer–Supported Catalytic Asymmetric Sharpless Dihydroxylations of Olefins", Eur. J. Org. Chem, 1998, pp. 21–27.

*Alessandro Mandoli et al*, "A first example of macromolecular Ti(IV) Lewis acid in the catalytic enantioselective Mukaiyama reaction", Tetrahedron: Asymmetry, 1998, 9, pp. 1479–1482.

*Juliane Beliczey et al*, "Novel ligands derived from S–tyrosine for the enantioselective addition of diethylzinc to aldehydes", Tetrahedron: Asymmetry, 1997, vol. 8, No. 10, pp. 1529–1530.

*Marcel Felder et al*, "A polymer–enlarged homogeneously soluble oxazaborolidine catalyst for the asymmetric reduction of ketones by borane", Tetrahedron: Asymmetry, 1997, vol. 8, No. 12, pp. 1975–1977.

*Christoph Koellner et al*, "Dendrimers Containing Chiral Ferrocenyl Diphosphine Ligands for Asymmetric Catalysis", J. Am Chem. Soc., 1998, 120, pp. 10274–10275.

*Filippo Minutolo et al*, "Polymer–Bound Chiral(Salen)Mn(III) Complex as Heterogeneous Catalyst in Rapid and Clean Enantioselective Epoxidation of Unfunctionalised Olefins", Tetrahedron Letters, 1996, vol. 37, No. 19, pp. 3375–3378.

*Torsten Malmstroem et al*, "A novel chiral water–soluble phosphine ligand based on a water–soluble acrylic acid salt", Chem. Commun., 1996, pp. 1135–1136.

*Dennis J. Gravert et al*, "Organic Synthesis on Soluble Polymer Supports: Liquid–Phase Methodologies", Chem. Rev., 1997, 97, pp. 489–509.

*K.E. Geckler et al*, "Soluble Polymer Supports for Liquid–Phase Synthesis", Advances in Polymer Science, 1995, vol. 121, pp. 31–79.

*Georg Hochwimmer et al*, "6,6'–Bisfunctionalized 2,2'–bipyridines as metallo–supramolecular initiators for the living polymerization of oxazolines", Macromol. Rapid Commun., 19, 1998, pp. 309–318.

*Stephen J. Shuttleworth et al*, "Functionalised Polymers: Recent Developments and New Applications in Synthetic Organic Chemistry", Synthesis, 1997, pp. 1217–1239.

*Iwao Ojima*, "The Chemistry of Organic Silicon Compounds", 1989, pp. 1479–1526.

*Sebastian Rissom et al*, "Asymmetric reduction of acetophenone in membrane reactors: comparison of oxazaborolidine and alcohol dehydrogenase catalysed processes", Tetrahedron: Asymmetry, 1999, 10, pp. 923–928.

*Matthew J. Palmer et al*, "Asymmetric transfer hydrogenation of C=O and C=N bonds", Tetrahedron: Asymmetry, 10, 1999, pp. 2045–2061.

*Ryoji Noyori et al*, "Asymmetric Transfer Hydrogenation Catalyzed by Chiral Ruthenium Complexes", Acc. Chem. Res., 1997, 30, pp. 97–102.

*Ryoji Noyori*, "Asymmetric catalysis in organic synthesis", 1994, pp. 122–254.

*Udo Kragl et al*, "Applied Homogeneous Catalysis with Organometallic Compounds", 1996, pp. 832–843.

*G. Bell et al*, "Engineering Processes for Bioseperations", 1994, pp. 135–165.

\* cited by examiner

MOLECULAR WEIGHT-ENLARGED LIGANDS FOR ASYMMETRIC, HOMOGENEOUSLY SOLUBLE HYDROGENATION CATALYSTS, PROCESS FOR THE PRODUCTION THEREOF AND USE

BACKGROUND OF THE INVENTION

1. Field of the Invention

The present invention relates to molecular weight-enlarged ligands for catalysts and their use for the asymmetric, homogeneous hydrogenation of double bonds.

2. Discussion of the Background

Catalytically active species for the asymmetric, homogeneous hydrogenation of double bonds are extremely advantageous for the industrial synthesis of organic substances. This is particularly the case due to their improved recyclability, which helps keep manufacturing costs low for synthetically produced products.

Molecular weight-enlarged catalysts for homogeneous enantioselective hydrogenation are known in the literature. J. Am. Chem. Soc. (1998), 120, 9481 et seq. addresses the problem of producing soluble molecular weight enlargements, inter alia, for hydrogenation catalysts. Wandrey et al have also reported the use of a molecular weight-enlarged hydrogenation catalyst in a membrane reactor (Angew. Chem. (1990), 102, 445 et seq.). U.S. Pat. No. 5,777,062 describes homogeneously soluble polymer-enlarged ligands for hydrogenation catalysts. The monomeric ligands are bound in this case to the polymer backbone via urethane or urea linkers.

The catalysts described above have problems, for example, in that it is difficult to separate the catalysts from the product with regard to the membrane used, and the catalysts become inactivated over the course of the reaction. These and other problems associated with the catalysts described above have not been adequately been resolved to date, and thus there is still a requirement for novel catalyst systems which make it possible to perform continuous processes catalytically.

SUMMARY OF THE INVENTION

Accordingly, one object of the present invention is to provide a homogenous soluble hydrogenation catalyst that is readily separable from the product of the hydrogenation.

Another object of the present invention is to provide a molecular weight-enlarged ligand for preparing such a catalyst.

Another object of the present invention is to provide a method for preparing such ligands and catalysts.

Another object of the invention is to provide a method for the asymmetric, homogenous hydrogenation of unsaturated compounds using such catalysts.

These and other objects have been achieved by the present invention, the first embodiment of which provides a molecular weight-enlarged, homogeneously soluble ligand, which includes:

an average molecular weight of at least 1000 g/mol;
a molecular weight-enlarging polymer;
optionally, a polymer linker; and
at least one homochiral active center;
wherein the active center is bound to the molecular weight-enlarging polymer through the polymer linker or is bound directly to the molecular weight-enlarging polymer; and
wherein the active center is selected from the group including compounds having the formulas in the following table, and combinations thereof:

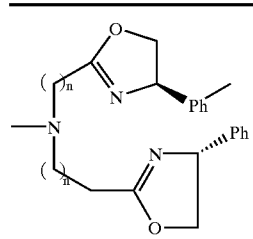

n = 0–5

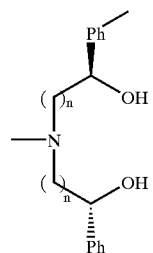

n = 0–5

-continued

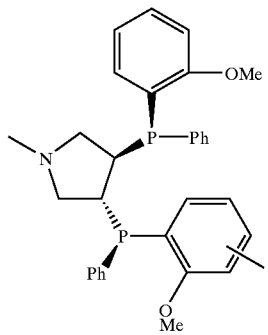

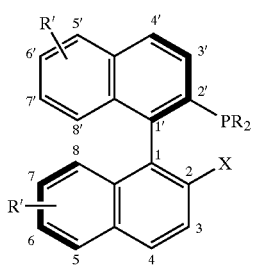

R = cyclohexyl or
(C$_6$–C$_{18}$) aryl
R' = H or polymer linkage
through said polymer
linker or directly to said
molecular weight
enlarging polymer
X = PR$_2$ or OMe

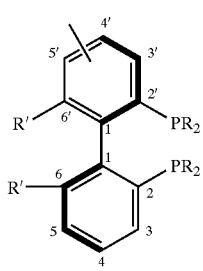

R = cyclohexyl or
(C$_6$–C$_{18}$) aryl
R' = CH$_3$, OMe, CF$_3$, H or tert. Bu

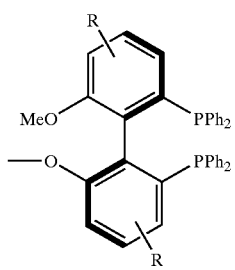

R = H, CF$_3$, OMe or CH$_3$

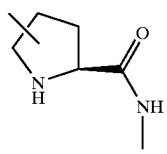

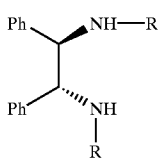

R = H, (C$_1$–C$_8$) alkyl or polymer linkage
through said polymer linker
or directly to said
molecular weight
enlarging polymer

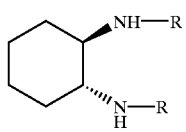

R = H, (C$_1$–C$_8$) alkyl or polymer linkage
through said polymer linker
or directly to said
molecular weight
enlarging polymer -continued

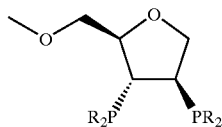

R = cyclohexyl or
(C$_6$–C$_{18}$) aryl

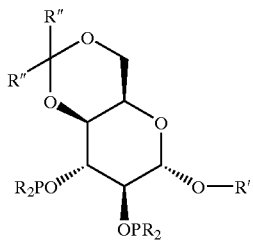

R = cyclohexyl or
(C$_6$–C$_{18}$) aryl
R' = (C$_1$–C$_8$) alkyl,
(C$_7$–C$_{19}$) aralkyl or
(C$_6$–C$_{18}$) aryl or
polymer linkage
through said polymer linker
or directly to said
molecular weight
enlarging polymer
R" = (C$_1$–C$_8$) alkyl or
polymer linkage
through said polymer linker
or directly to said
molecular weight
enlarging polymer

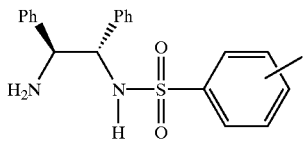

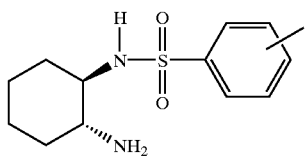

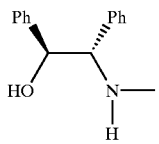

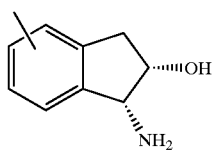

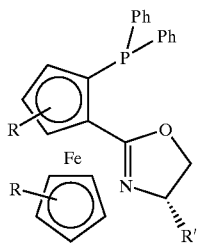

R = H or polymer linkage
through said polymer linker
or directly to said
molecular weight
enlarging polymer
R' = (C$_1$–C$_8$) alkyl,
(C$_7$–C$_{19}$) aralkyl or
(C$_6$–C$_{18}$) aryl -continued

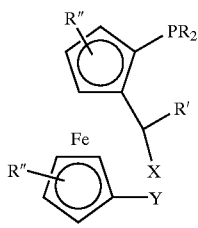

R = cyclohexyl or
(C$_6$–C$_{18}$) aryl
R' = (C$_1$–C$_8$) alkyl, H or
polymer linkage
through said polymer linker
or directly to said
molecular weight
enlarging polymer
R" = H or polymer linkage
through said polymer linker
or directly to said
molecular weight
enlarging polymer
X = NR'$_2$, NR'H, OMe or OAc
Y = Pr$_2$ or H

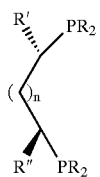

R = cyclohexyl or
(C$_6$–C$_{18}$) aryl
R' = (C$_1$–C$_8$) alkyl,
(C$_6$–C$_{18}$) aryl or H
R" = polymer linkage
through said polymer linker
or directly to said
molecular weight
enlarging polymer
n = 0, 1 or 2

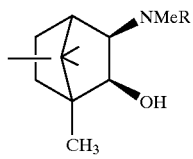

R = H, (C$_1$–C$_8$) alkyl or polymer linkage
through said polymer linker
or directly to said
molecular weight
enlarging polymer

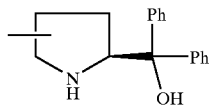

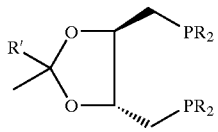

R = cyclohexyl or
(C$_6$–C$_{18}$) aryl
R' = H, (C$_1$–C$_8$) alkyl or
(C$_6$–C$_{18}$) aryl

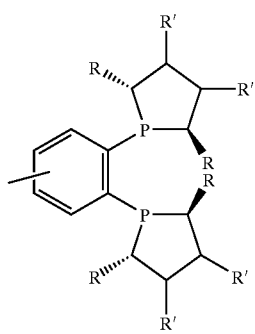

R = (C$_1$–C$_8$) alkyl
R' = H, O-(C$_1$–C$_8$) alkyl,
O-(C$_7$–C$_{19}$) aralkyl,
O-(C$_6$C$_{18}$aryl or OH

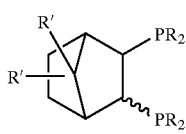

R = cyclohexyl or
(C$_6$–C$_{18}$) aryl
R' = H or polymer linkage
through said polymer linker
or directly to said
molecular weight
enlarging polymer -continued

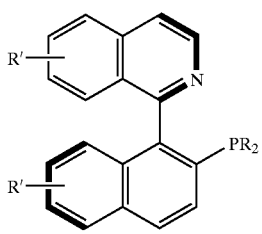

R = cyclohexyl or
(C$_6$–C$_{18}$) aryl
R' = H or polymer linkage
through said polymer linker
or directly to said
molecular weight
enlarging polymer

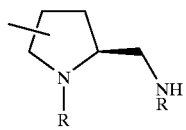

R = H, (C$_1$–C$_8$) alkyl,
(C$_7$–C$_{19}$) aralkyl or
polymer linkage
through said polymer linker
or directly to said
molecular weight
enlarging polymer

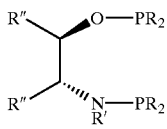

R = cyclohexyl or
(C$_6$–C$_{18}$) aryl
R' = H, (C$_1$–C$_8$) alkyl or
polymer linkage
through said polymer linker
or directly to said
molecular weight
enlarging polymer
R''= H, (C$_1$–C$_8$) alkyl,
(C$_7$–C$_{19}$) aralkyl,
(C$_6$–C$_{18}$) aryl,
polymer linkage
through said polymer linker
or directly to said
molecular weight
enlarging polymer

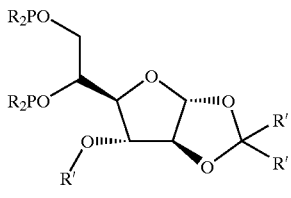

R = cyclohexyl or
(C$_6$–C$_{18}$) aryl
R' = H, (C$_1$–C$_8$) alkyl,
(C$_7$–C$_{19}$) aralkyl,
(C$_6$–C$_{18}$) aryl or
polymer linkage through
said polymer linker
or directly to said
molecular weight
enlarging polymer

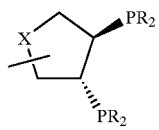

R = cyclohexyl or
(C$_6$–C$_{18}$) aryl
X = CH$_2$, O, S, PR or NH

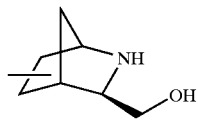

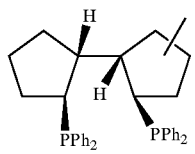

-continued

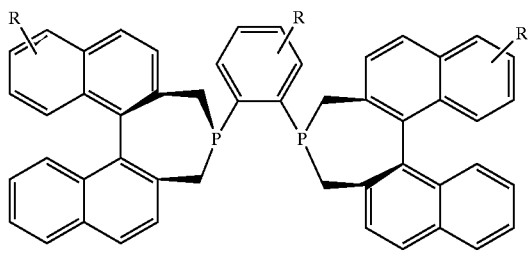

R = H or polymer linkage through said polymer linker or directly to said molecular weight enlarging polymer

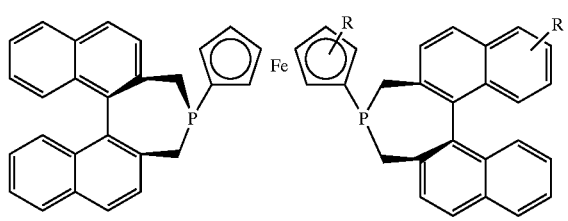

R = H, polymer linkage through said polymer linker or directly to said molecular weight enlarging polymer

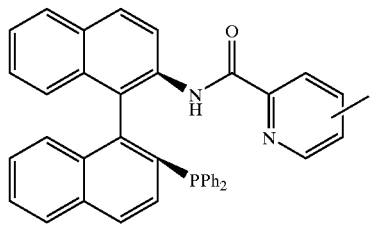

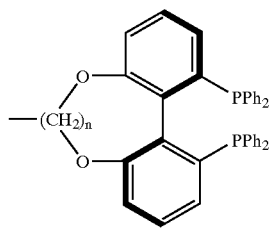

(n = 1–6)

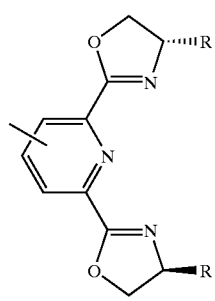

R = (C$_1$–C$_8$) alkyl,
(C$_7$–C$_{19}$) aralkyl,
(C$_6$–C$_{18}$) aryl or
polymer linkage through said polymer linker or directly to said molecular weight enlarging polymer

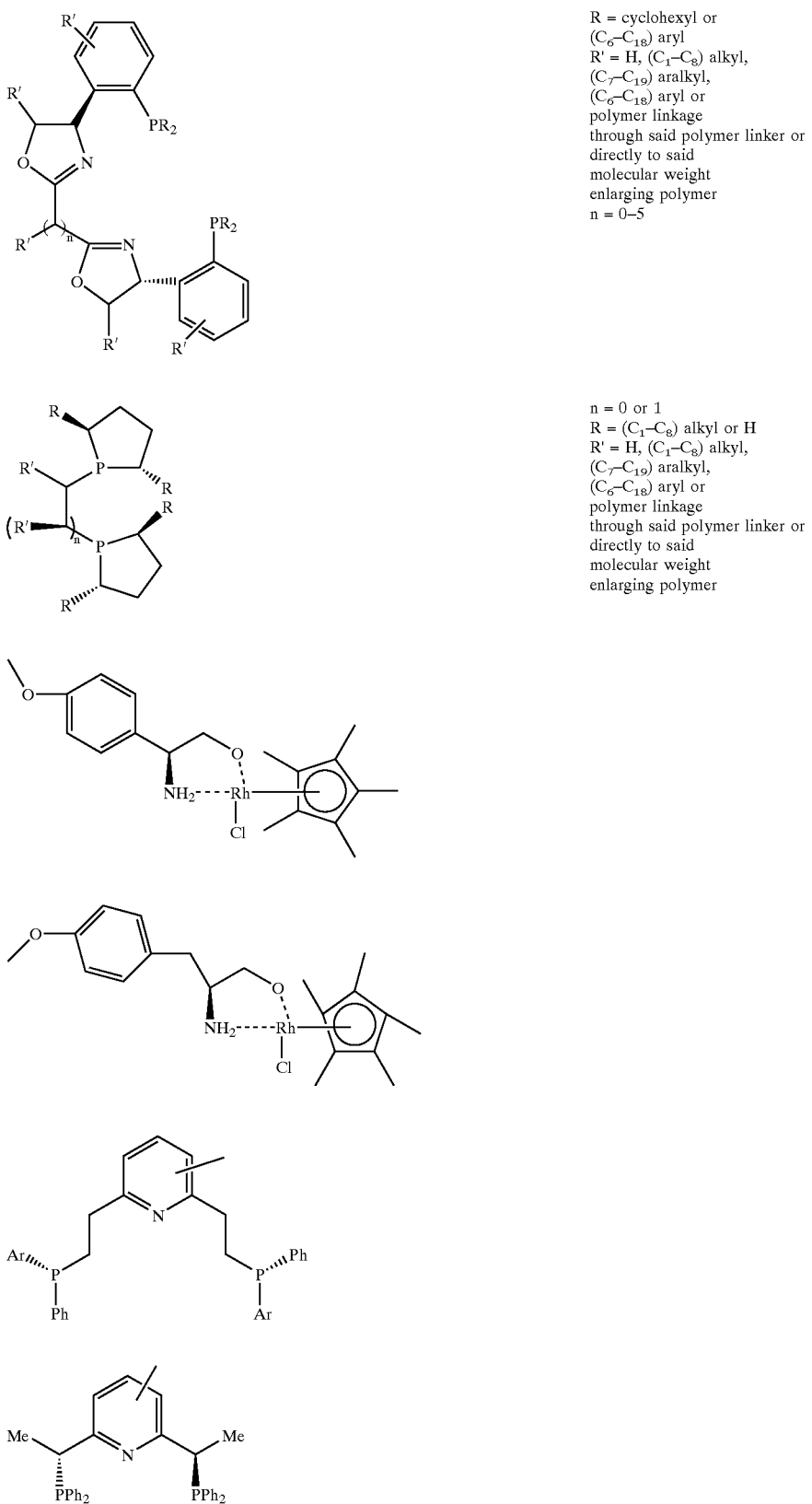
R = cyclohexyl or
($C_6$–$C_{18}$) aryl
R' = H, ($C_1$–$C_8$) alkyl,
($C_7$–$C_{19}$) aralkyl,
($C_6$–$C_{18}$) aryl or
polymer linkage
through said polymer linker or
directly to said
molecular weight
enlarging polymer
n = 0–5
n = 0 or 1
R = ($C_1$–$C_8$) alkyl or H
R' = H, ($C_1$–$C_8$) alkyl,
($C_7$–$C_{19}$) aralkyl,
($C_6$–$C_{18}$) aryl or
polymer linkage
through said polymer linker or
directly to said
molecular weight
enlarging polymer -continued

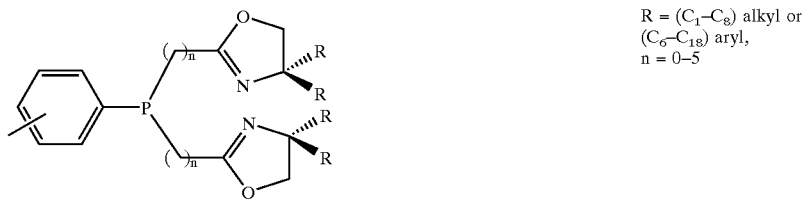

R = (C₁–C₈) alkyl or
(C₆–C₁₈) aryl,
n = 0–5

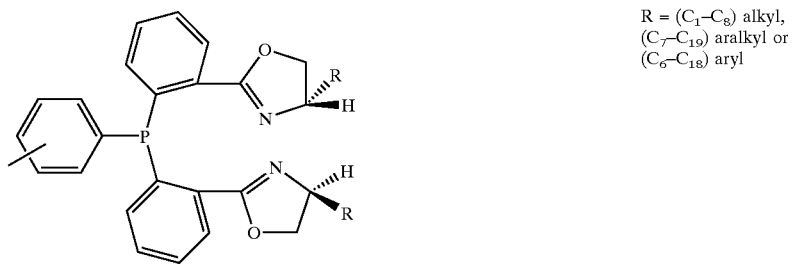

R = (C₁–C₈) alkyl,
(C₇–C₁₉) aralkyl or
(C₆–C₁₈) aryl

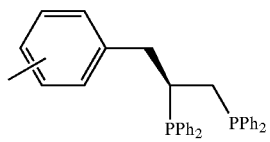

polymer
OR', OAc, NR'₂ or NH₂

R = cyclohexyl,
(C₆–C₁₈) aryl
R' = (C₁–C₈) alkyl,
(C₆–C₁₈) aryl or
polymer linkage
through said polymer linker or
directly to said
molecular weight
enlarging polymer
R" = H, (C₁–C₈) alkyl,
(C₇–C₁₉) aralkyl,
(C₆–C₁₈) aryl,
polymer linkage
through said polymer linker or
directly to said
molecular weight
enlarging

polymer

R = cyclohexyl or (C₆–C₁₈) aryl
R' = (C₁–C₈) alkyl,
(C₆–C₁₈) aryl or
polymer linkage
through said polymer linker or
directly to said
molecular weight
enlarging polymer
R" = H, (C₁–C₈) alkyl,
(C₆–C₁₈) aryl, OR',
OAc, NR'₂, NH₂,
polymer linkage through said
polymer linker or
directly to said
molecular weight
enlarging -continued

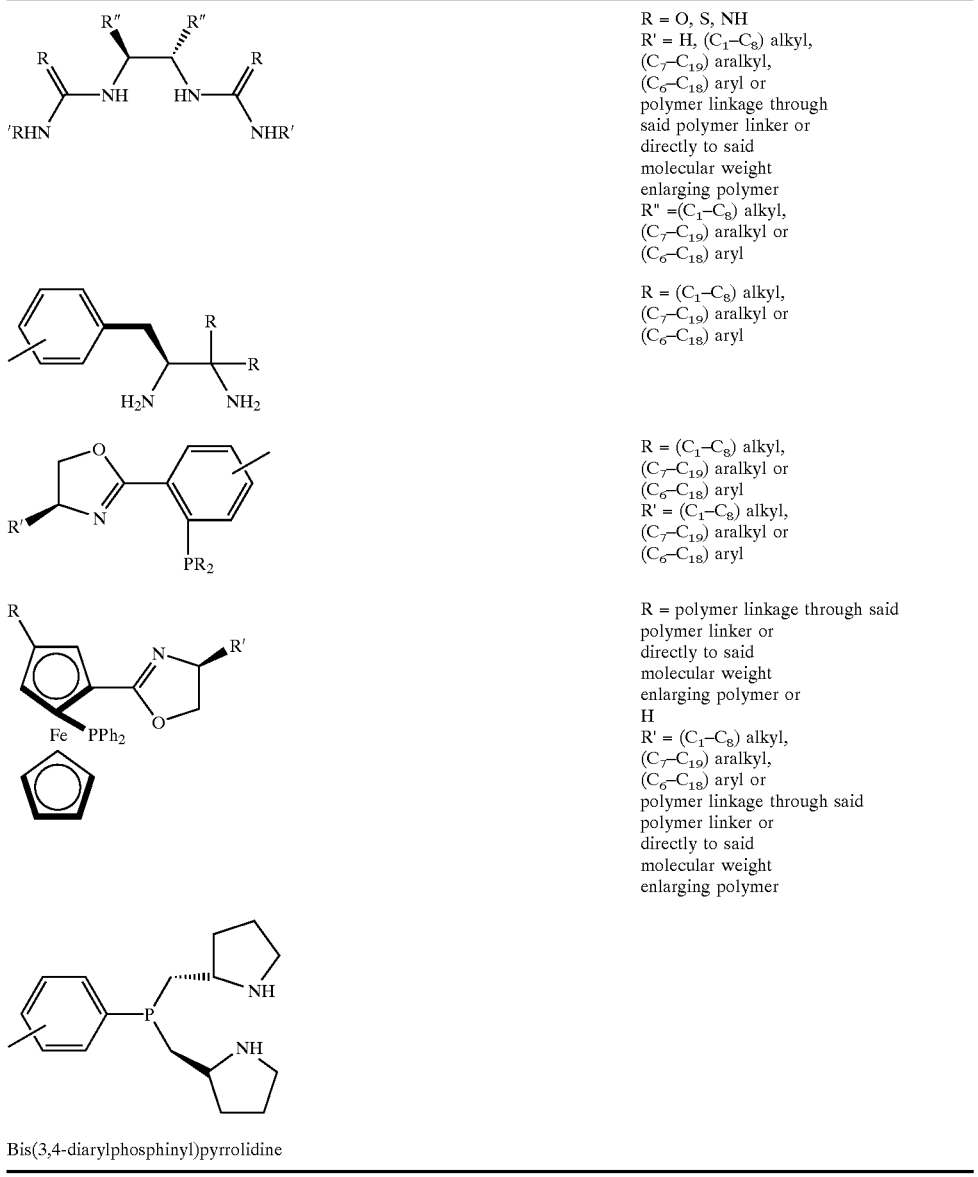

Bis(3,4-diarylphosphinyl)pyrrolidine wherein a line extending from said formulas of said active center represents a bond of a binding site both for the molecular weight enlarging polymer or for the optional polymer linker;

wherein the polymer linker is selected from the group including compounds of the formulae a)–g):

| a) | —Si(R$_2$)— | |
| b) | —(SiR$_2$—O)$_n$— | n = 1–10000; |
| c) | —(CHR—CHR—O)$_n$— | n = 1–10000; |
| d) | —(X)$_n$— | n = 1–20; |
| e) | Z—(X)$_n$— | n = 0–20; |
| f) | —(X)$_n$—W | n = 0–20; and |
| g) | Z—(X)$_n$—W | n = 0–20; | wherein

R is H, (C$_1$–C$_8$) alkyl, (C$_6$–C$_{18}$) aryl, (C$_7$–C$_{19}$) aralkyl, or ((C$_1$–C$_8$) alkyl)$_{1-3}$-(C$_6$–C$_{18}$) aryl;

X is (C$_6$–C$_{18}$) arylene, (C$_1$–C$_8$) alkylene, (C$_1$–C$_8$) alkenylene, ((C$_1$–C$_8$) alkyl)$_{1-3}$-(C$_6$–C$_{18}$) arylene, or (C$_7$–C$_{19}$) aralkylene;

Z is C(=O)O—, C(O)NH—, C(=O)—, NR, O, CHR, CH$_2$, C=S, S, or PR, Z being bound directly to the molecular weight enlarging polymer;

W is C(=O)O—, C(=O)NH—, C(=O)—, NR, O, CHR, CH$_2$, C=S, S, or PR, Z being bound directly to the active center.

Another embodiment of the present invention provides a catalyst, that includes at least one of the above-noted ligands and one or more metals or metal ions selected from the group including Ru, Rh, Ir, Pd, Ni, Pt, Co, ions thereof, and mixtures thereof.

Another embodiment of the present invention provides a process for the production of a ligand, which includes a step selected from the group including (a)–(c):

(a) binding a homochiral active center to a monomer directly or through a linker to provide a modified monomer, and polymerizing the modified monomer in the presence of one or more unmodified monomers;

(b) binding a homochiral active center to a polymer, either directly or through a linker; and (c) carrying out either of steps (a) or (c) and further polymerizing the resulting polymer with one or more additional polymers, wherein the one or more additional polymers optionally includes one or more homochiral active centers.

Another embodiment of the present invention provides a process for producing one or more enantiomerically enriched organic compounds, which includes:

performing a reaction on a starting material that includes at least one non-chiral site to convert the non-chiral site into a chiral site;

wherein the reaction is performed in the presence of a catalyst for the reaction, the catalyst including at least one of the above-noted molecular weight-enlarged ligands.

DESCRIPTION OF THE PREFERRED EMBODIMENTS

Figure 1:
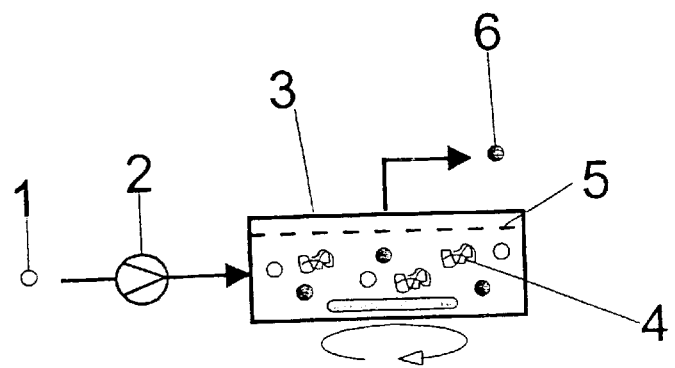
FIG. 1 shows a membrane reactor with dead end filtration. The substrate 1 is transferred by means of a pump 2 into the reaction chamber 3, which comprises a membrane 5. In addition to the solvent, the stirred reaction chamber contains the catalyst 4, the product 6 and unreacted substrate 1. Low molecular weight 6 is primarily filtered out through the membrane 5.

Various other objects, features and attendant advantages of the present invention will be more fully appreciated as the same becomes better understood from the following detailed description when considered in connection with the accompanying drawings in which like reference characters designate like or corresponding parts throughout the several views.

By use of the present invention, it becomes possible to use further, very readily recyclable, polymer-enlarged hydrogenation catalysts for industrial organic synthesis.

The indicated bonds in the chemical structures stated in the table are preferred binding sites both for the polymer and for the optional linker. More preferably, one of the indicated possibilities for binding may be adequate. Even more preferably, the possibility of polymer linkage is stated for specific residues in the right hand column of the table. This should also be taken to apply to the possibility of binding the linkers.

In the above table showing the structures of the homochiral active centers (hereinafter also referred to as the "table"), the ranges of carbon numbers given for the respective R, R', and R" and in the accompanying description for the linker, each range of carbon numbers for the alkyl, aryl, aralkyl, alkylene, arylene, alkenylene, and aralkenylene includes all values and subranges therebetween, including $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$ and $C_{19}$.

The first five general structures in the above table are particularly preferable active centers.

The molecular weight-enlarged, homogeneously soluble hydrogenation catalysts may preferably be synthesised as follows from the molecular weight enlargement, optional linker and active center.

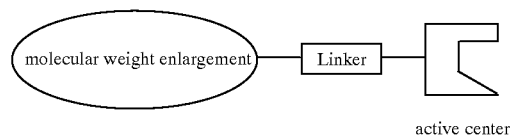

active center

Molecular Weight Enlargement (Molecular Weight-Enlarged Polymer):

For the purposes of the invention, the molecular weight enlargement may be freely selected. The enlargement is preferably selected in view of considerations of practicability, cost and by technical issues (e.g., retention capacity, solubility etc.). Especially preferable polymer enlargements for catalysts are described in Reetz et al., Angew. Chem. 1997, 109, 1559 et seq.; Seebach et al., Helv. Chim Acta 1996, 79, 1710 et seq.; Kragl et al., Angew. Chem. 1996, 108, 684 et seq.; Schurig et al., Chem. Ber./Recueil 1997, 130, 879 et seq.; Bolm et al., Angew. Chem. 1997, 109, 773 et seq.; Bolm et al. Eur. J. Org. Chem. 1998, 21 et seq.; Baystone et al. in Speciality Chemicals 224 et seq.; Salvadori et al., Tetrahedron: Asymmetry 1998, 9, 1479; Wandrey et al., Tetrahedron: Asymmetry 1997, 8, 1529 et seq.; ibid. 1997, 8, 1975 et seq.; Togni et al. J. Am. Chem. Soc. 1998, 120, 10274 et seq., Salvadori et al., Tetrahedron Lett. 1996, 37, 3375 et seq.; WO 98/22415; DE 19910691.6; Janda et al., J. Am. Chem. Soc. 1998, 120, 9481 et seq.; Andersson et al., Chem. Commun. 1996, 1135 et seq.; Janda et al., Soluble Polymers 1999, 1, 1; Janda et al., Chem. Rev. 1997, 97, 489; Geckler et al., Adv. Polym. Sci. 1995, 121, 31; White et al., in "The Chemistry of Organic Silicon Compounds", Wiley, Chichester, 1989, 1289; Schuberth et al., Macromol. Rapid Commun. 1998, 19, 309; Sharma et al., Synthesis 1997, 1217; "Functional Polymers" ed.: R. Arshady, ASC, Washington, 1996; "Praktikum der Makromolekularen Stoffe", D. Braun et al., VCH-Wiley, Weinheim 1999, the relevant contents of each of which are hereby incorporated by reference.

Preferred molecular weight-enlarging polymers for binding the ligands (active centers) are polyacrylates, polyvinylpyrrolidinones, polysiloxanes, polybutadienes, polyisoprenes, polyalkanes, polystyrenes, polyoxazolines or polyethers (PEG, PEP) or mixtures thereof. For the purposes of the invention, mixtures are taken to mean the fact that individual polymers of differing origin are polymerized together to yield block polymers. Random mixtures of monomers in the polymer are also possible.

Polyacrylates, polysiloxanes, polystyrenes and/or polyethers are very particularly preferred for this purpose.

The molecular weight-enlarging polymers preferably exhibit an average molecular weight in the range from 1,000–1,000,000, more preferably from 5,000–500,000, and particularly preferably from 5,000–300,000 g/mol, which ranges include all values and subranges therebetween.

Linkers:

A linker may be inserted between the actual catalyst or ligand (active center) and the polymer enlargement. The catalyst may, however, also be bound directly to the polymer enlargement.

The purpose of the linker is to provide a space between the active center and polymer in order to mitigate or eliminate any mutual interactions which are disadvantageous to the reaction.

For the purposes of the invention, these actual active hydrogenation catalysts are accordingly bound to the polymer enlargement directly or preferably via a linker selected from the above-stated group.

Further preferred linkers are shown in the following scheme:

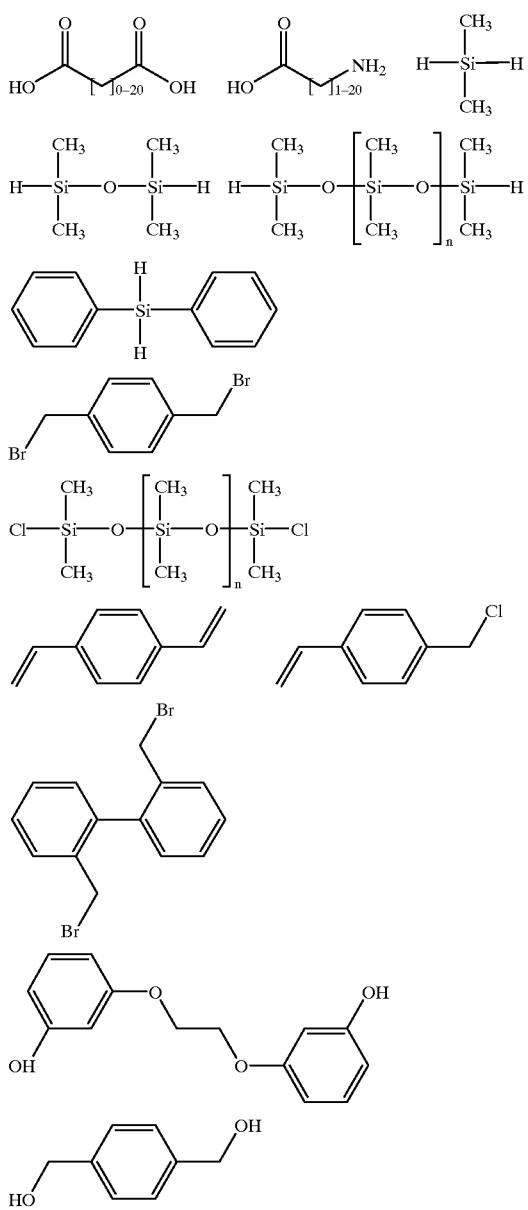

Very particularly preferred linkers include, for example, 1,4'-biphenyl, 1,2-ethylene, 1,3-propylene, PEG (2–10), α,ω-siloxanylene or 1,4-phenylene and α,ω-1,4-bisethylenebenzene, or linkers which are obtainable from siloxanes of the general formula I:

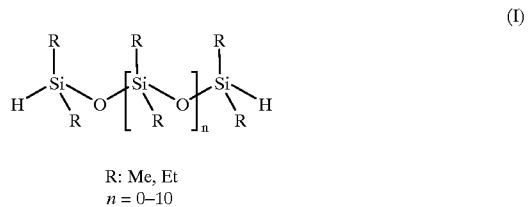

R: Me, Et
$n = 0-10$

The linkers, preferably, may readily be bound to any double bonds present in the polymers and suitable functional groups of the active centers under hydrosilylation conditions (see, e.g., the review of the hydrosilylation reaction by Ojima in The Chemistry of Organic Silicon Compounds, 1989 John Wiley & Sons Ltd., 1480–1526, the entire contents of which are hereby incorporated by reference).

Active Centers:

For the purposes of the invention, an active center (homochiral active center) is taken to mean the actual low molecular weight ligand which has hitherto normally been used for the hydrogenation. As explained above, this may be attached to the molecular weight enlargement directly or via a linker as stated above.

Preferable active centers include those which firstly ensure elevated optical yield combined with the fastest possible hydrogenation, so resulting in an elevated throughput. The active center is preferably sufficiently insensitive to oxidation by atmospheric oxygen such that it is not necessary to use degassed solvent and adequate storage stability of the ligands is provided.

An extremely preferred active center is the 1,2-diphosphine of the following structure

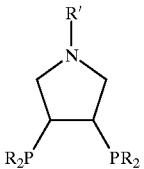

in which

R' denotes H, $(C_1-C_8)$ alkyl, $(C_6-C_{18})$ aryl, $(C_7-C_{19})$ aralkyl,

R denotes cyclohexyl, $(C_6-C_{18})$ aryl.

It is within the scope of the invention that, in accordance with the knowledge of a person skilled in the art, the above-stated constituents of the molecular weight-enlarged catalyst (molecular weight enlargement, linker, active center) may be combined at will with regard to optimizing the manner in which the reaction is performed.

Combining Molecular Weight Enlargement with Linker/Active Center:

Two preferable methods for attaching the linkers/active centers to the molecular weight enlargement include:

a) the catalytically active center may be bound with a bound linker or directly to a monomer and the latter is polymerized in the presence of one or more unmodified monomers, or b) the catalytically active center is bound via a linker or directly to the molecular weight enlargement.

It is optionally possible to prepare polymers according to a) or b), which may be further copolymerized with other polymers, which include other catalytically active centers and may be produced according to a) or b).

Preferably, the number of linkers/active centers per monomer in the polymer is such that as many catalytically active centers as possible should be located on a polymer, such that conversion per polymer is consequently increased. On the other hand, however, the centers are preferably spaced apart in such a manner that any mutual negative influence on reactivity (TOF, selectivity) is minimised or does not occur. The spacing between linkers/active centers in the polymer should thus preferably be in the range from 1–200 monomer units, more preferably 5–25 monomer units, and most preferably 10 to 15 monomer units, which ranges include all values and subranges therebetween.

Preferably, the sites on the polymer or on the monomer to be polymerized which are used for binding the linker/active center are those which may readily be functionalised or permit an existing functionality to be used for binding. Heteroatoms or unsaturated carbon atoms are thus preferably suitable for binding the components.

For example, in the case of styrene/polystyrene, the aromatic rings which are present may be used as attachment points to the linkers/active centers. Functionalities may readily be linked to these aromatic rings, preferably in positions 3, 4, 5, particularly preferably in position 4, by means of standard aromatic chemistry. It is, however, also advantageous to incorporate, for example, an already functionalised monomer into the mixture to be polymerized and, after polymerization, to bind the linker to the functionalities present in the polystyrene. Compounds which are advantageously suitable for this purpose are, for example, para-hydroxy-, para-chloromethyl or para-aminostyrene derivatives.

In the case of polyethers, the existing terminal OH group is preferred for binding to the linkers/active centers by ester or ether formation or by oxidation of this group to form an acid group with subsequent esterification or amide formation (Nagel et al., Chem. Ber. 1986, 119, 3326–3343; Oehme et al. DE 19730657.8). The relevant contents of each of these references are hereby incorporated by reference.

In the case of polyacrylates, an acid group or ester group is in each case present in the monomer constituent, to which the linker or the active center may be bound preferably via an ester or amide bond before or after polymerization.

Polysiloxanes as a molecular weight enlargement are preferably synthesised such that, in addition to dimethylsilane units, hydromethylsilane units are also present, which are modified by alkyl residues which comprise double bonds or heteroatoms. The linkers/active centers may then be coupled to these sites.

They may preferably be bound to the functionalities under consideration in the polymer under hydrosilylation conditions (review of the hydrosilylation reaction by Ojima in The Chemistry of Organic Silicon Compounds, 1989 John Wiley & Sons Ltd., 1480–1526) the relevant contents being hereby incorporated by reference. Suitable polysiloxanes modified in this manner are known from the literature ("Siloxane polymers and copolymers" White et al., in S. Patai (ed.), "The Chemistry of Organic Silicon Compounds", Wiley, Chichester, 1989, 46, 2954; C. Wandrey et al. TH:Asymmetry 1997, 8, 1975, the relevant contents of each of which being hereby incorporated by reference).

Preferably, the active center is bound to the linker or the molecular weight-enlarging polymer with one or more of the open bonds or polymer linkages in the compounds in the table.

Combining Linker with Active Center:

The details relating to joining the polymer to the linker/active center also apply synonymously to binding the active center to the linker.

The linker/polymer may accordingly preferably be bound to the active centers via heteroatoms or certain functionalities thereof, such as C=O, $CH_2$, O, N, S, P, Si, B, wherein preferably ether/thioether bonds, amine bonds, amide bonds are linked or esterification, alkylation, silylation and addition reactions are performed on double bonds.

Thus, where heteroatoms are present in the active centers which are not involved in complexing the metal, the active centers are preferably bound via these atoms, such as for example in general structures 1–3 of the table via the amino function.

In general structure 4 of the table, linkage in positions 5-7 or 5'-7' is particularly suitable, with position 6 or 6' being extremely preferred.

In general structure 5 of the table, position 4-6 or 4'-6' is highly suitable. Position 5 or 6 or 5' or 6' may particularly readily be selected.

The following structures, in which the values for a and b are statistical averages, are extremely preferred. The values are advantageously 1 for a and 2 to 50, preferably 5 to 25 for b (scheme 1), which ranges include all values and subranges therebetween, including 3, 6, 7, 9, 10, 12, 14, 16, 19, 21, and 23 for b.

Scheme 1

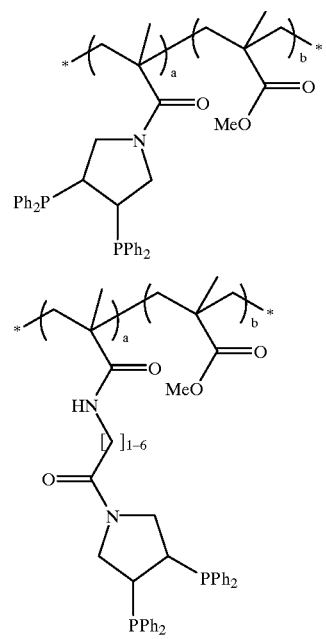

The present application also provides a process for the production of ligands according to the invention, which is distinguished in that a) the catalytically active center is bound with a bound linker or directly to one or more monomers and the latter is polymerized in the presence of unmodified monomers, b) the catalytically active center is bound via a linker or directly to the finished polymer, or c) polymers according to a) or b) are prepared and copolymerized with other polymers which may include catalytically active centers.

The ligands according to the invention are preferably used for the production of enantiomerically enriched organic compounds. The use thereof in a membrane reactor is very particularly preferred. As a result, syntheses normally performed in batch processes may proceed semi-continuously or continuously, which, from a cost standpoint, is particularly advantageous for an industrial process. The ligands according to the invention or catalysts produced therefrom are used in the membrane reactor in an analogous manner to the process described in DE 199 10 691.6; and Wandrey et al., Tetrahedron Asymmetry 1999, 10, 923–928, the relevant contents of each of which being hereby incorporated by reference.

The ligands according to the invention are preferably used in the production of enantiomerically enriched organic compounds. In particular, the present invention provides a method for the selective production of enantiomerically enriched organic compounds (an enantiomeric reaction that generates one enantiomer of a compound selectively over the opposite enantiomer).

Figure 2:
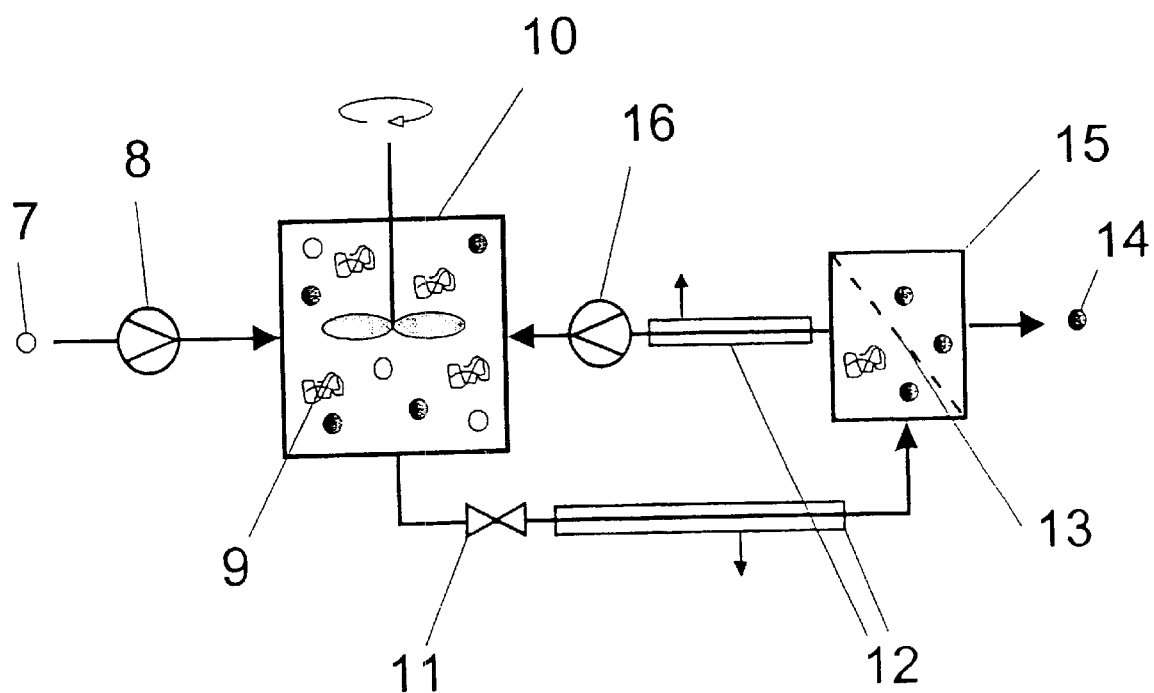
FIG. 2 shows a membrane reactor with crossflow filtration. In this case, the substrate 7 is transferred by means of the pump 8 into the stirred reaction chamber, which also contains solvent, catalyst 9 and product 14. A stream of solvent is established by means of the pump 16, which stream passes via an optionally present heat exchanger 12 into the crossflow filtration cell 15. It is here that the low molecular weight product 14 is separated by means of the membrane 13. High molecular weight catalyst 9 is then passed with the solvent stream optionally through the valve 11, optionally again through a heat exchanger 12, back to the reactor 10.

Continuous operation may be performed as desired using the crossflow filtration mode (FIG. 2) or as dead end filtration (FIG. 1).

In the case of dead end operation, catalyst and solvent are initially introduced into the reactor and the dissolved substrate is then apportioned, wherein a source of hydrogen must simultaneously be present. The substrate is enantioselectively reduced by means of the catalyst and then discharged from the membrane reactor with the solvent stream via the ultrafiltration membrane.

In the case of crossflow operation, the reaction solution containing solvent, substrate, product and catalyst as well as a hydrogen source, is passed in front of a membrane, across which a pressure differential prevails.

In both cases, the dissolved substrate is apportioned at such a rate and the pressure potential across the particular membrane is adjusted such that the discharged solution predominantly contains enantioselectively hydrogenated product. Both process variants have been described in Engineering processes for Bioseparations, ed.: L. R. Weatherley, Butterworth-Heinemann, 1994, pp. 135–165, the relevant contents of which being hereby incorporated by reference.

The hydrogen source for the hydrogenation according to the invention may be gaseous hydrogen which is introduced into the system during the reaction. In this case, the entire apparatus is preferably located in a hydrogen atmosphere at hydrogenation pressure, such that the same hydrogen pressure prevails on both sides of the filtration membrane and hydrogen thus cannot diffuse out of the system via the membrane.

Preferably, the reaction pressure conditions across the membrane may more readily be adjusted as mentioned above. An elevated pressure differential before and after the membrane would result in outgassing on the filtrate side, which could result in equipment problems. Moreover, increased passage of hydrogen through the membrane could accelerate fouling.

This method is preferably performed at hydrogen pressures of 0.1–20, more preferably of 0.2–0.5 Mpa, which ranges include all values and subranges therebetween, including 0.75, 1, 3, 4, 6, 8, 9, 11, 12, 14, 15, 17and 19 Mpa.

In another preferred development, hydrogenation is performed by the transfer hydrogenation method. This method is described, for example, in the literature ("Asymmetric transfer hydrogenation of C=O and C=N bonds", M. Wills et al. Tetrahedron: Asymmetry 1999, 10, 2045; "Asymmetric transfer hydrogenation catalysed by chiral ruthenium complexes", R. Noyori et al. Acc. Chem. Res. 1997, 30, 97; "Asymmetric catalysis in organic synthesis", R. Noyori, John Wiley & Sons, New York, 1994, p.123; "Transition metals for organic Synthesis", eds. M. Beller, C. Bolm, Wiley-VCH, Weinheim, 1998, vol. 2, p. 97; "Comprehensive Asymmetric Catalysis", eds.: Jacobsen, E. N.; Pfaltz, A.; Yamamoto, H., Springer-Verlag, 1999, the relevant contents of each of which are hereby incorporated by reference).

Preferred hydrogen-producing substrates used in this case are alcohols, formates, cyclohexene or cyclohexadiene, very particularly preferably formic acid in the presence of a base, such as for example triethylamine.

C=C, C=N or C=O double bonds may preferably be hydrogenated with the assistance of the ligands according to the invention.

The invention also provides a molecular weight-enlarged catalyst which is synthesised from a ligand according to the invention and metals or metal ions selected from the group Ru, Rh, Ir, Pd, Ni, Pt, Co, ions thereof, and combinations thereof.

For the purposes of the invention, a molecular weight-enlarged ligand/catalyst should be taken to mean such a ligand/catalyst in which the molecular weight-enlarging polymer is covalently bonded to the active center.

($C_1$–$C_8$) alkyl should be taken to mean methyl, ethyl, n-propyl, isopropyl, n-butyl, isobutyl, sec-butyl, tert-butyl, pentyl, hexyl, heptyl or octyl, including all bond isomers.

A ($C_6$–$C_{18}$) aryl residue is taken to mean an aromatic residue having 6 to 18 C atoms. These in particular include compounds such as phenyl, naphthyl, anthryl, phenanthryl, biphenyl residues. These may be mono- or polysubstituted with ($C_1$–$C_8$) alkoxy, ($C_1$–$C_8$) haloalkyl, OH, Cl, $NH_2$, $NO_2$. The residue may also contain one or more heteroatoms such as N, O, S.

($C_1$–$C_8$) alkoxy is a ($C_1$–$C_8$) alkyl residue, which is bound via an oxygen atom to the molecule concerned.

($C_1$–$C_8$) haloalkyl is a ($C_1$–$C_8$) alkyl residue substituted with one or more halogen atoms. Chlorine and fluorine may in particular be considered as halogen atoms.

A ($C_7$–$C_{19}$) aralkyl residue is a ($C_6$–$C_{18}$) aryl residue bound to the molecule via a ($C_1$–$C_8$) alkyl residue.

For the purposes of the invention, the term acrylate is also taken to mean methacrylate.

For the purposes of the invention, a membrane reactor is taken to mean any reaction vessel in which the catalyst is enclosed in a reactor, while low molecular weight substances are supplied to the reactor or are able to leave it. The membrane may here be incorporated directly into the reaction chamber or be installed outside the chamber in a separate filtration module, in which the reaction solution flows continuously or intermittently through the filtration module and the retentate is returned to the reactor. Suitable embodiments are described, inter alia, in WO98/22415 and in Wandrey et al. in Jahrbuch 1998, Verfahrenstechnik und Chemieingenieurwesen, VDI pp. 151 et seq.; Wandrey et al. in Applied Homogeneous Catalysis with Organometallic Compounds, Vol. 2, VCH 1996, pp. 832 et seq.; Kragl et al., Angew. Chem. 1996, 6, 684 et seq., the relevant contents of each of which being hereby incorporated by reference. The reaction may be performed batchwise, semi-continuously, or continuously.

The chemical structures shown relate to all possible stereoisomers which may be obtained by modifying the configuration of the individual chiral centers, axes or planes, i.e. any possible diastereomers, as well as any optical isomers (enantiomers) included therein.

EXAMPLES

Having generally described this invention, a further understanding can be obtained by reference to certain specific examples which are provided herein for purposes of illustration only and are not intended to be limiting unless otherwise specified.

Acylation to Yield MMA-PYRPHOS (3,4-bis(diphenylphosphino)-N-isobutenonepyrrolidine):

1.54 g of methacryloyl chloride in 35 mL of toluene are slowly added dropwise at 0° C. to a solution of 5.00 g of 3,4-bis(diphenylphosphino)pyrrolidine in 20 mL of toluene and 20 mL of 2N NaOH. Once the reaction is complete, the phases are separated and the aqueous phase extracted with toluene. The combined organic phases are washed in succession with dilute hydrochloric acid and saturated NaCl solution. After drying over magnesium sulfate, the solvent is stripped out under a vacuum. 5.7 g of the desired product are obtained as a white powder. NMR analysis confirms the identity of the desired product.

Polymerization to Yield PMMA-Pyrphos:

20.0 mmol of methyl methacrylate (MMA) and 0.1 mmol of azoisobutyronitrile (AIBN) are added to a solution of 1.0 mmol of MMA-Pyrphos in methyl isobutyl ketone. After heating to 80° C. over 20 h, the product is precipitated in petroleum ether and filtered out. 1.5 g of the desired polymer are obtained as a white powder. NMR analysis confirms the identity of the desired product.

Asymmetric Hydrogenation:

A solution of 182 mg of PMMA-Pyrphos and 2.00 g of acetamidocinnamic acid in 60 mL of MeOH/H$_2$O (5:1) is stirred at 50° C. and 50 bar H$_2$ until no further hydrogen is absorbed.

The pressure vessel is then depressurised and the reaction solution extracted with ether. After drying the organic phase over magnesium sulfate, the solvent is stripped out under a vacuum. 1.8 g of N—Ac-phenylalanine are obtained with selectivity of ee=40%. HPLC analysis confirms the identity of the desired compound.

Production of Polyether-Pyrphos:

1. Chloroformic Acid Esters

All operations were performed under argon in order to exclude air and moisture.

A solution of 1.32 g (1.1 mmol) of Brij 35 (C$_{12}$H$_{25}$(OCH$_2$CH$_2$)$_{32}$OH) or of 5.24 g (1.1 mmol) of Synperonic PE/P 103 (HO(CH$_2$CH$_2$O)$_{17}$(CH(CH$_3$)CH$_2$O)$_{56}$(CH$_2$CH$_2$O)$_{17}$H) in 10 ml of dichloromethane is slowly added dropwise to 90 ml of a solution of phosgene (1.7662 mmol/ml) cooled to −40° C. and adjusted to 0° C. within 5 h. The excess phosgene is removed with appropriate safety precautions by concentrating the solution to approx. 3 ml and the remaining residue is directly further used.

2. Reaction of the Chloroformic Acid Esters with Pyrphos ((R,R)-3,4-bis(diphenylphosphino)pyrrolidine)

1.1 mmol of the corresponding chloroformic acid ester in 3 ml of CH$_2$Cl$^2$ are added under an argon atmosphere and with stirring at 0° C. to a solution of 0.483 g (1.1 mmol) of Pyrphos and 0.18 ml (1.32 mmol) of triethylamine in 10 ml of dichloromethane. The reaction mixture is stirred for three hours at 0 to 5° C. and then concentrated. The residue is redissolved in 10 ml of ether and left to stand overnight to crystallise the triethylamine hydrochloride. On the next day, the mixture is inert-filtered, the filtrate concentrated and the residue dried under a vacuum at 50° C.

Analysis of the Derivative (I) Derived from Brij 35:
C$_{87}$H$_{143}$NO$_{25}$P$_2$ (1664.82)

Calc.: C=62.76%; H=8.65%; N=0.84%; P=3.72% Found: C=63.57%; H=8.48%; N=1.26%; P=4.11%

$^{31}$P=−11.8 ppm (CDCl$_3$) Yield=1.34 g (80.5%)

Analysis of Derivative (II) Derived from the Block Copolymer Synperonic PE/P 103: C$_{294}$H$_{524}$N$_2$O$_{94}$P$_4$ (5714.51):

Calc.: C=61.96%; H=9.27%; N=0.49%; P=2.17% Found: C=62.13%; H=9.15%; N=0.91%; P=2.48%

$^{31}$P=−11.8 ppm (CDCl$_3$) Yield=5.27 g (92.2%)

| Hydrogenation of (Z)-α-acetamidocinnamic acid methyl ester in water and methanol with the catalyst system: [Rh(COD)$_2$]BF$_4$ + amphiphilised ligands (I) and (II): H$_2$, 1 bar; 25° C. | | | | |
|---|---|---|---|---|
| Medium | | t½ (min) | % eeS | Conversion, % |
| | Rh:I:substrate | | | |
| H$_2$O | 1:1:100 | ~10 h | 88 | 98 (Rh°↓) |
| | Rh:II:substrate | | | |
| H$_2$O | 2:1:100 | ~12 h | 80 | 94 (Rh°↓) |
| H$_2$O | 1:0.5:100 | ~11 h | 83 | 96 (Rh°↓) |
| Methanol | 1:0.5:100 | 248 min | 88 | 100 |
| H$_2$O + SDS (Rh:SDS = 1:2) | 1:0.5:100 | 9 h | 79 | 97 |

SDS: sodium dodecyl sulfate

In a new batch, 1 mmol of substrate, 0.0005 mmol of ligand (II), 0.001 mmol of Rh(COD)$_2$BF$_4$ was dissolved in 15 ml of methanol. Hydrogenation was performed in the first case at 10 bar, RT and 24 h, in the second case at 20 bar, RT and 24 h. Result: case 1) 88.6% ee; case 2) 89.5% ee.

This application is based on German patent application DE 100 02 976.0, filed Jan. 24, 2000, the entire content of which are hereby incorporated by reference.

Having now fully described the invention, it will be apparent to one of ordinary skill in the art that many changes and modifications can be made thereto without departing from the spirit or scope of the invention as set forth herein.

What is claimed is:

1. A molecular weight-enlarged, homogeneously soluble ligand, comprising:

a molecular weight-enlarging polymer;

optionally, a polymer linker; and at least one homochiral active center;

wherein said active center is bound to said molecular weight-enlarging polymer through said polymer linker or is bound directly to said molecular weight-enlarging polymer; and wherein said active center is selected from the group consisting of compounds having the formulas in the following table, and combinations thereof:

X is (C$_6$–C$_{18}$) arylene, (C$_1$–G$_8$) alkylene, (C$_1$–C$_8$) alkenylene, ((C$_1$–C$_8$) alkyl$_{1-3}$-(C$_6$–C$_{18}$) arylene, or (C$_7$–C$_{19}$) aralkylene;

Z is C(=O)O—, C(=O)NH—, C(=O)—, NR, O, CHR, CH$_2$, C=S, S, PR, Z being bound directly to said molecular weight enlarging polymer; and W is C(=O)O—, C(=O)NH—, C(=O)—, NR, O, CHR, CH$_2$, C=S, S, PR, W being bound directly to said active center;

wherein the molecular weight-enlarging polymer is a member selected from the group consisting of polyacrylates, polyvinylpyrrolidinones, polysiloxanes, polybutadienes, polyisoprenes, polyalkanes, polystyrenes, polyoxazolines and mixtures thereof.

2. The ligand according to claim 1, wherein said homochiral active center is a ligand on a metal or metal ion selected from the group consisting of Ru, Rh, Ir, Pd, Ni, Pt, Co, and ions thereof.

3. The ligand according to claim 1, wherein said homochiral active center is a catalytically active center.

4. The ligand according to claim 1, wherein said active center is bound to said polymer linker or said molecular weight-enlarging polymer one or more of the open bonds or polymer linkages in the compounds in said table.

5. A catalyst, comprising at least one ligand according to claim 1 and one or more metals or metal ions selected from the group consisting of Ru, Rh, Ir, Pd, Ni, Pt, Co, ions thereof, and mixtures thereof.

6. A process for the production of a ligand, comprising a step selected from the group consisting of (a)–(c):
   (a) binding a homochiral active center to a monomer directly or through a polymer linker to provide a modified monomer, and polymerizing said modified monomer in the presence of one or more unmodified monomers;
   (b) binding a homochiral active center to a polymer, either directly or through a polymer linker; and
   (c) carrying out either of steps (a) or (c) and further polymerizing the resulting polymer with one or more additional polymers, wherein said one or more additional polymers optionally comprise one or more homochiral active centers;
   wherein said one or more homochiral active centers are selected from the group consisting of compounds having the formulas in the following table, and combinations thereof:

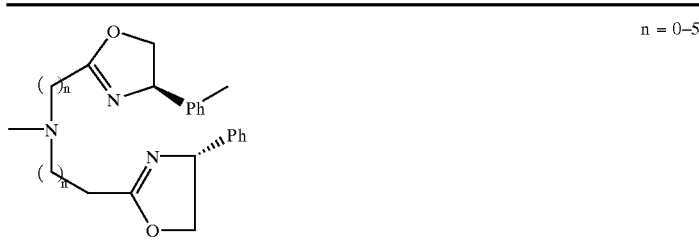

n = 0–5

n = 0–5

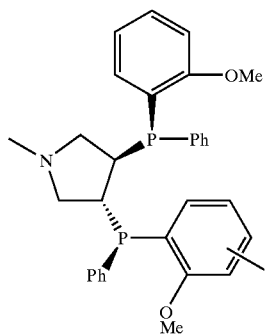

R = cyclohexyl or (C$_6$–C$_{18}$) aryl
R' = H, polymer linker or molecular weight enlarging polymer
X = PR$_2$ or OMe

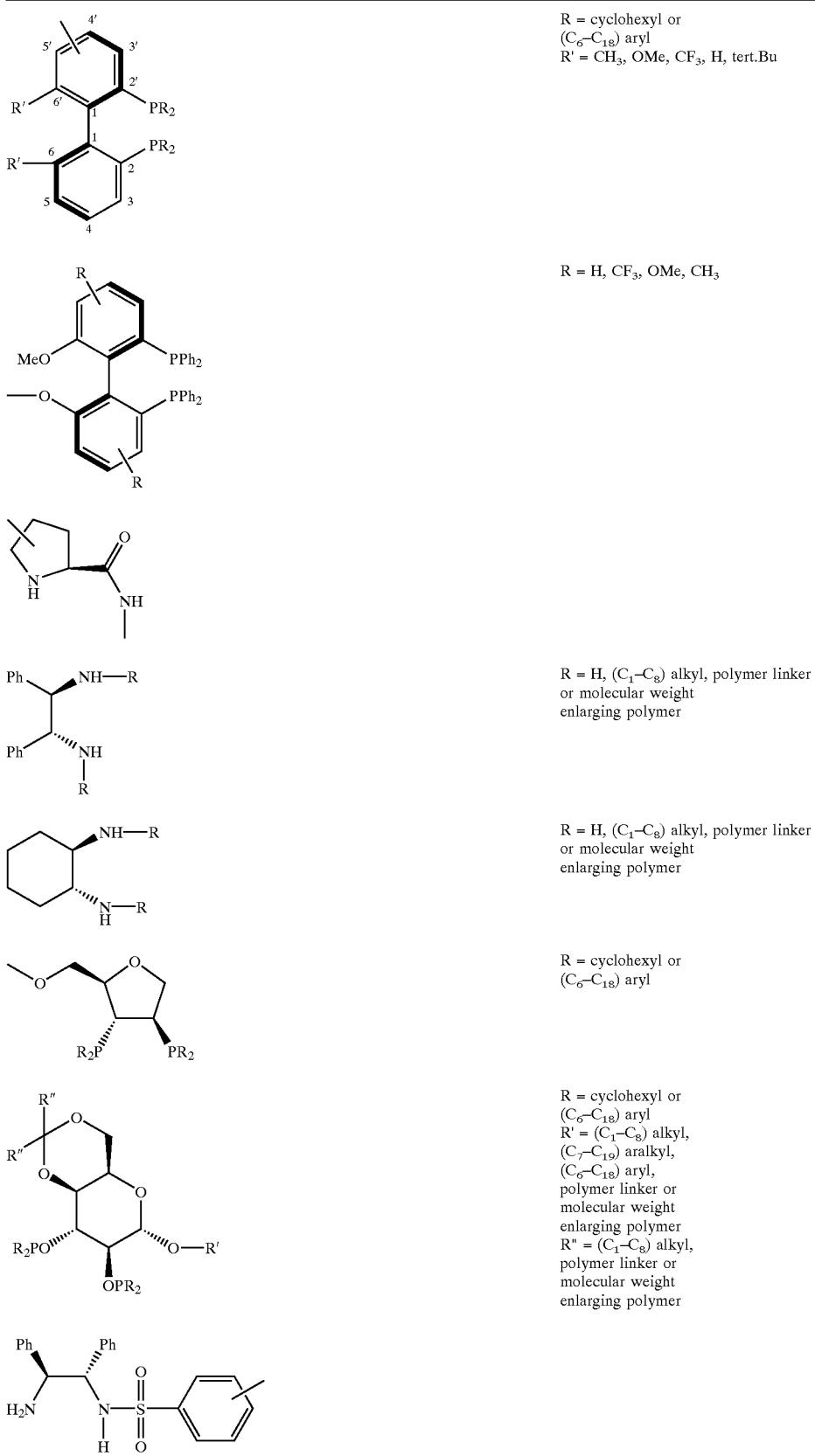

-continued

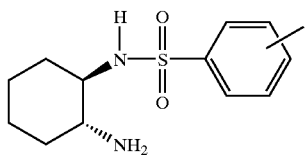

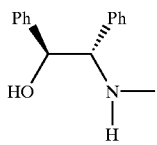

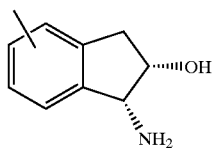

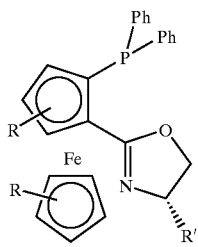

R = H, polymer linker
or molecular weight
enlarging polymer
R' = (C$_1$–C$_8$) alkyl,
(C$_7$–C$_{19}$) aralkyl or
(C$_6$–C$_{18}$) aryl

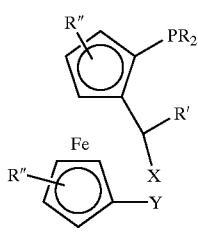

R = cyclohexyl or
(C$_6$–C$_{18}$) aryl
R' = (C$_1$–C$_8$) alkyl, H,
polymer linker or
molecular weight
enlrging polymer
R" = H, polymer linker or
molecular weight
enlarging polymer
X = NR'$_2$, NR'H, OMe or OAc
Y = PR$_2$ or H

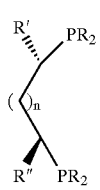

R = cyclohexyl or
(C$_6$–C$_{18}$) aryl
R' = (C$_1$–C$_8$) alkyl,
(C$_6$–C$_{18}$) aryl or H
R" = polymer linker
or molecular weight
enlarging polymer
n = 0, 1 or 2

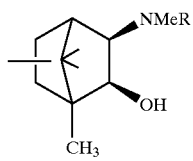

R = H, (C$_1$–C$_8$) alkyl, polymer linker
or molecular weight
enlarging polymer

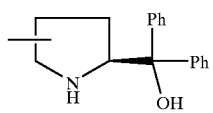

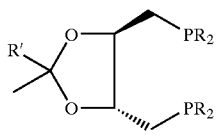

R = cyclohexyl or
(C$_6$–C$_{18}$) aryl
R' = H, (C$_1$–C$_8$) alkyl or
(C$_6$–C$_{18}$) aryl

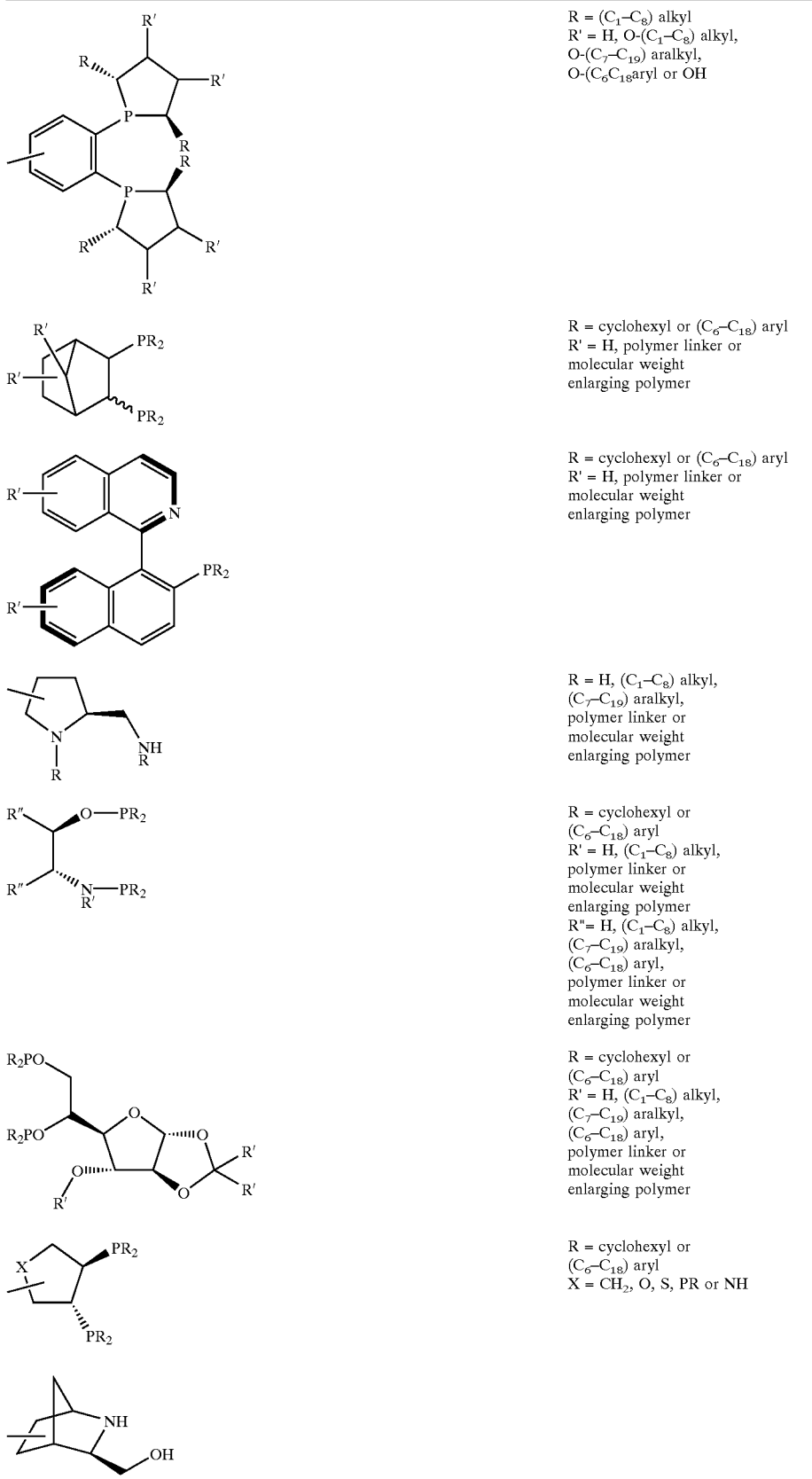

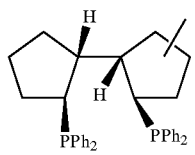
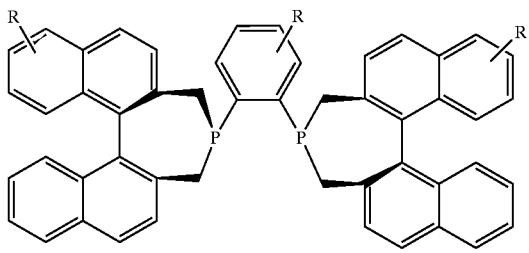
R = H, polymer linker or molecular weight enlarging polymer
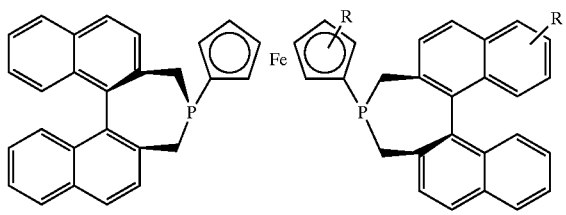
R = H, polymer linker or molecular weight enlarging polymer
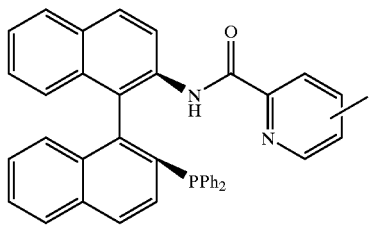
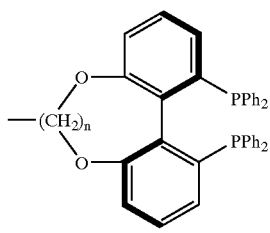
(n = 1–6)
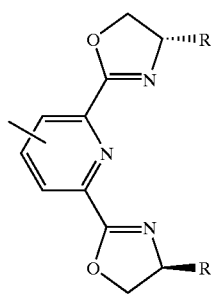
R = (C$_1$–C$_8$) aryl,
(C$_7$–C$_{19}$) aralkyl,
(C$_6$–C$_{18}$) aryl,
polymer linker or
molecular weight
enlarging polymer -continued
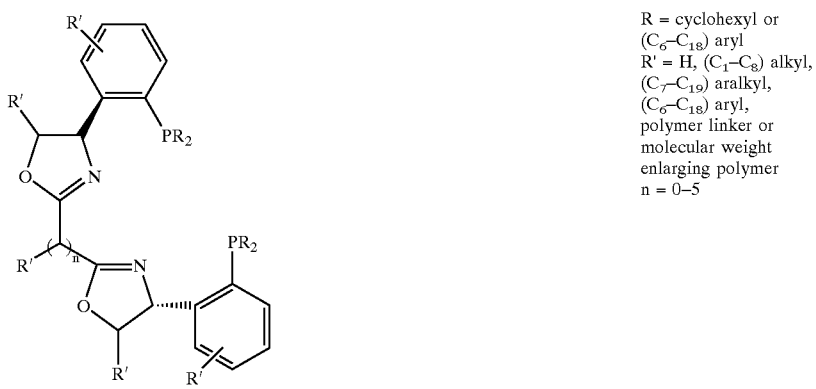
R = cyclohexyl or ($C_6$–$C_{18}$) aryl
R' = H, ($C_1$–$C_8$) alkyl, ($C_7$–$C_{19}$) aralkyl, ($C_6$–$C_{18}$) aryl, polymer linker or molecular weight enlarging polymer
n = 0–5
n = 0,1
R = ($C_1$–$C_8$) alkyl, H
R' = H, ($C_1$–$C_8$) alkyl, ($C_7$–$C_{19}$) aralkyl, ($C_6$–$C_{18}$) aryl, polymer linker or molecular weight enlarging polymer
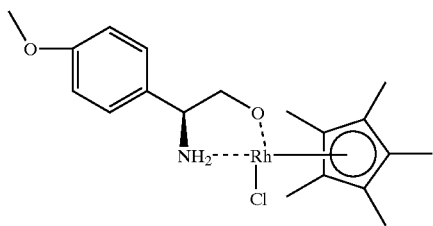
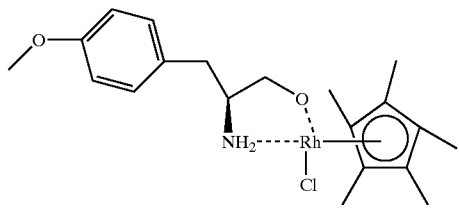
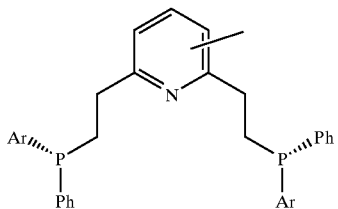
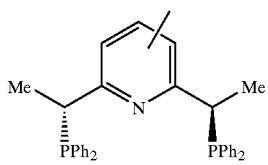

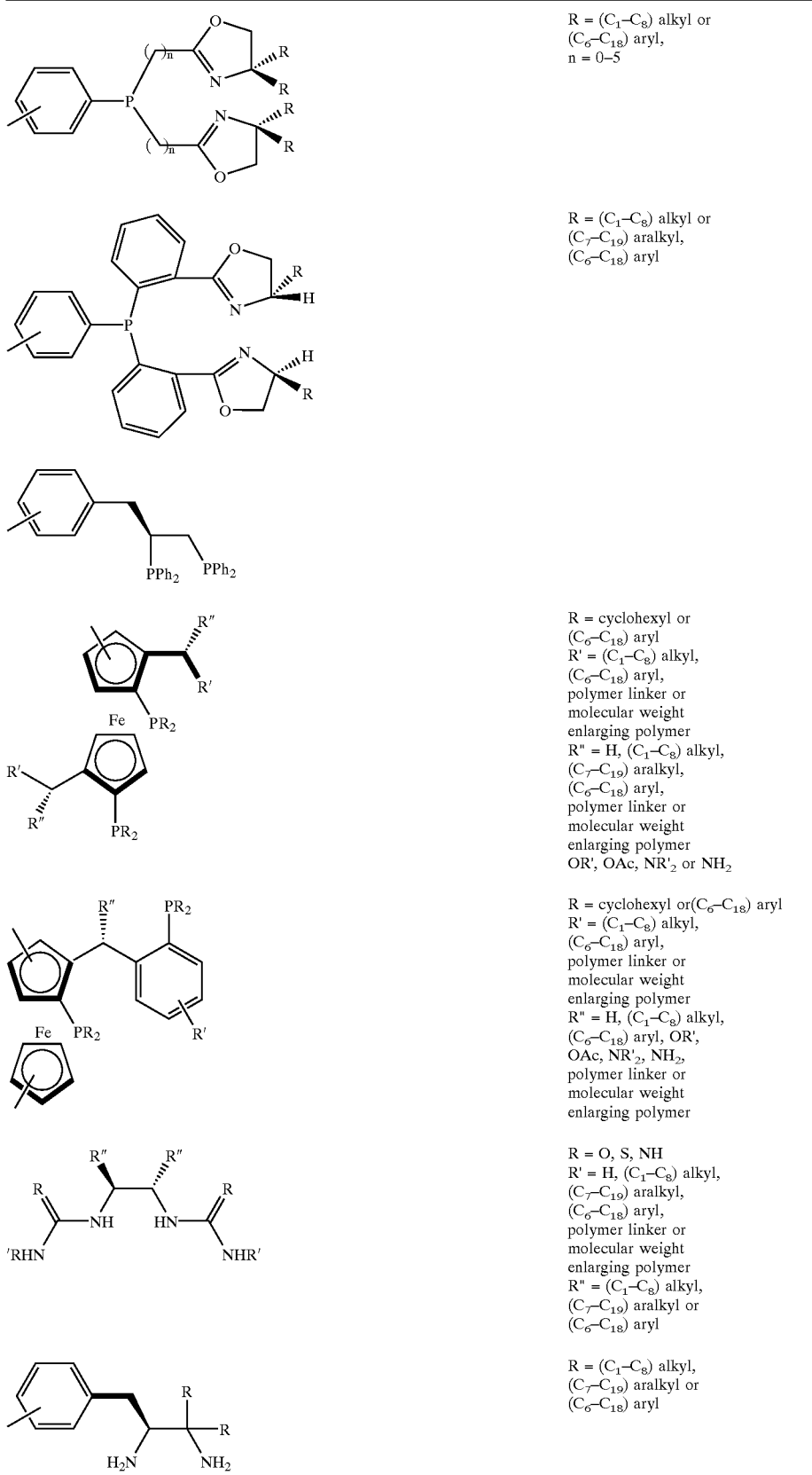

-continued

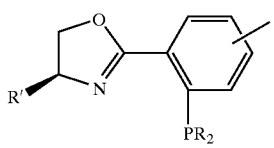

R = (C$_1$–C$_8$) alkyl,
(C$_7$–C$_{19}$) aralkyl or
(C$_6$–C$_{18}$) aryl
R' = (C$_1$–C$_8$) alkyl,
(C$_7$–C$_{19}$) aralkyl or
(C$_6$–C$_{18}$) aryl

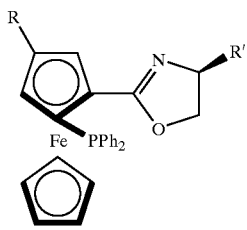

R = polymer linker or
molecular weight
enlarging polymer or H
R' = (C$_1$–C$_8$) alkyl,
(C$_7$–C$_{19}$) aralkyl,
(C$_6$–C$_{18}$) aryl,
polymer linker or
molecular weight
enlarging polymer

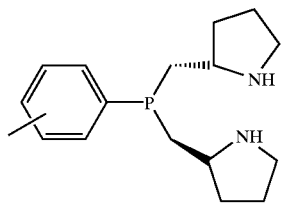

Bis(e,4-diarylphosphinyl)pyrrolidine wherein a line extending from said formulas of said one or more homochiral active centers represents a bond of a binding site both for the polymer or for the polymer linker;
wherein said polymer linker is a member selected from the group consisting of formulae a)–g):

| | | |
|---|---|---|
| a) | —Si(R$_2$)— | |
| b) | —(SiR$_2$—O)$_n$— | n = 1–10000; |
| c) | —(CHR—CHR—O)$_n$— | n = 1–10000; |
| d) | —(X)$_n$— | n = 1–20; |
| e) | Z—(X)$_n$— | n = 0–20; |
| f) | —(X)$_n$—W | n = 0–20; and |
| g) | Z—(X)$_n$—W | n = 0–20; | wherein
R is H, (C$_1$–C$_8$) alkyl, (C$_6$–C$_{18}$) aryl, (C$_7$–C$_{19}$) aralkyl, or ((C$_1$–C$_8$) alkyl)$_{1-3}$-(C$_6$–C$_{18}$) aryl;
X is (C$_6$–C$_{18}$) arylene, (C$_1$–C$_8$) alkylene, (C$_1$–C$_8$) alkenylene, ((C$_1$–C$_8$) alkyl$_{1-3}$-(C$_6$–C$_{18}$) arylene, or (C$_7$–C$_{19}$) aralkylene;
Z is C(=O)O—, C(=O)NH—, C(=O)—, NR, O, CHR, CH$_2$, C=S, S, PR, Z being bound directly to said polymer; and
W is C(=O)O—, C(=O)NH—, C(=O)—, NR, O, CHR, CR$_2$, C=S, S, PR, W being bound directly to said homochiral active center;
wherein the polymer is a member selected from the group consisting of polyacrylates, polyvinylpyrrolidinones, polysiloxanes, polybutadienes, polyisoprenes, polyalkanes, polystyrenes, polyoxazolines and mixtures thereof.

7. The process according to claim 6, wherein said polymer is a member selected from the group consisting of polysiloxanes, polystyrenes and polyacrylates and mixtures thereof.

8. The process according to claim 5, further comprising contacting said ligand with one or more metals or metal ions selected from the group consisting of Ru, Rh, Ir, Pd, Ni, Pt, Co, ions thereof, and mixtures thereof.

9. The process according to claim 6, wherein said homochiral active center is bound to said polymer linker or said polymer with one or more of the bonds or polymer linkages in the compounds in said table.

10. A process comprising producing one or more enantiomerically enriched organic compounds, comprising:
performing a reaction on a starting material comprising at least one non-chiral site to convert said non-chiral site into a chiral site;
wherein said reaction is performed in the presence of a catalyst for said reaction, said catalyst comprising at least one molecular weight-enlarged ligand, which comprises:
a molecular weight-enlarging polymer;
optionally, a polymer linker; and
at least one homochiral active center;
wherein said active center is bound to said molecular weight-enlarging polymer through said polymer linker or is bound directly to said molecular weight-enlarging polymer; and
wherein said active center is selected from the group consisting of compounds having the formulas in the following table, and combinations thereof:

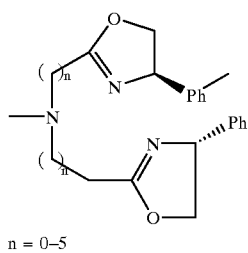

n = 0–5

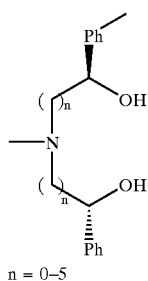

n = 0–5

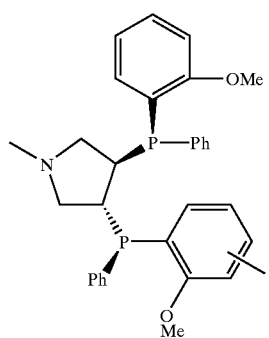

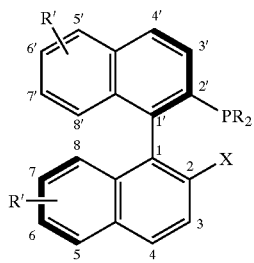

R = cyclohexyl or (C<sub>6</sub>–C<sub>18</sub>) aryl
R' = H, polymer linker or molecular weight enlarging polymer  X = PR<sub>2</sub> or OMe

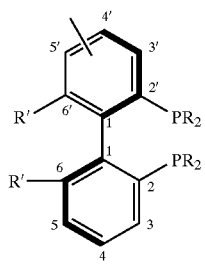

R = cyclohexyl or ($C_6$–$C_{18}$) aryl
R' = $CH_3$, OMe, $CF_3$, H or tert.Bu

-continued

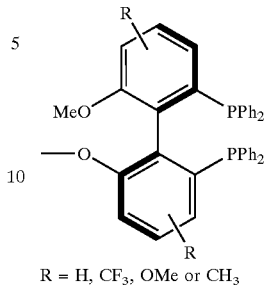

R = H, $CF_3$, OMe or $CH_3$

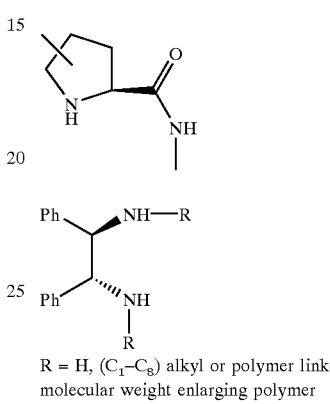

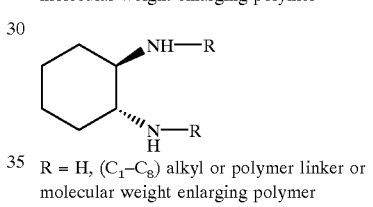

R = H, ($C_1$–$C_8$) alkyl or polymer linker or molecular weight enlarging polymer

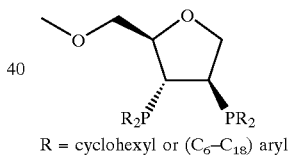

R = H, ($C_1$–$C_8$) alkyl or polymer linker or molecular weight enlarging polymer

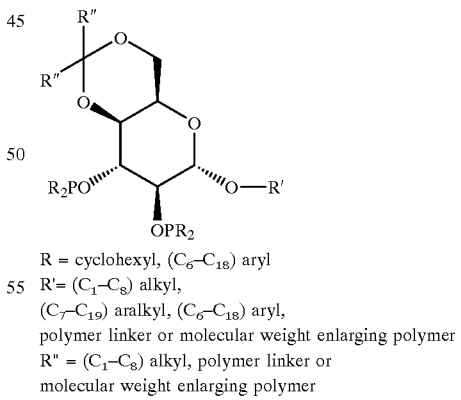

R = cyclohexyl or ($C_6$–$C_{18}$) aryl

R = cyclohexyl, ($C_6$–$C_{18}$) aryl
R' = ($C_1$–$C_8$) alkyl,
($C_7$–$C_{19}$) aralkyl, ($C_6$–$C_{18}$) aryl,
polymer linker or molecular weight enlarging polymer
R'' = ($C_1$–$C_8$) alkyl, polymer linker or molecular weight enlarging polymer

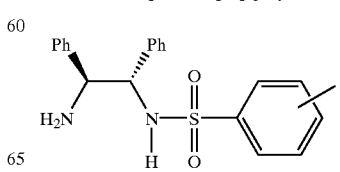

-continued

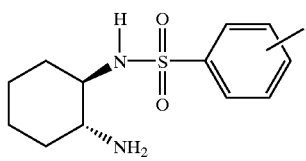

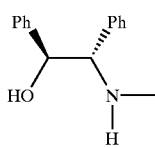

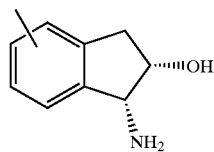

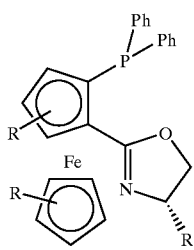

R = H, polymer linker or molecular weight enlarging polymer
R' = (C$_1$–C$_8$) alkyl, (C$_7$–C$_{19}$) aralkyl or (C$_6$–C$_{18}$) aryl

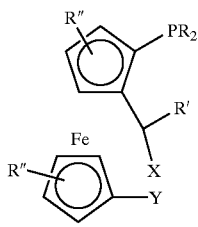

R = cyclohexyl or (C$_6$–C$_{18}$) aryl R' = (C$_1$–C$_8$) alkyl, H, polymer linker or molecular weight enlarging polymer R" H, polymer linker or molecular weight enlarging polymer
X = NR'$_2$, NR'H, OMe or OAc
Y = PR$_2$ or H

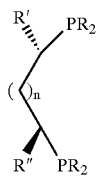

R = cyclohexyl or (C$_6$–C$_{18}$) aryl R' = (C$_1$–C$_8$) alkyl, (C$_6$–C$_{18}$) aryl or H R" = polymer linker or molecular weight enlarging polymer n = 0, 1 or 2

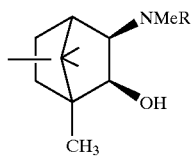

R = H, (C$_1$–C$_8$) alkyl, polymer linker or molecular weight enlarging polymer -continued

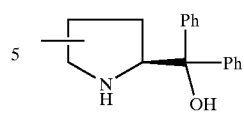

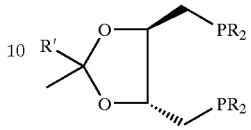

R = cyclohexyl or (C$_6$–C$_{18}$) aryl R' = H, C$_1$–C$_8$) alkyl or (C$_6$–C$_{18}$) aryl

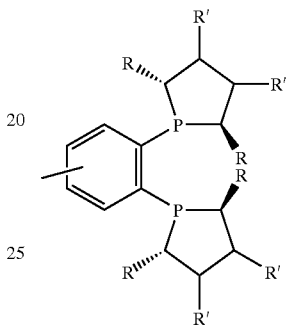

R = (C$_1$–C$_8$) alkyl R' = H, O—(C$_1$–C$_8$) alkyl, O—(C$_7$–C$_{19}$) aralkyl, O—(C$_6$–C$_{18}$) aryl or OH

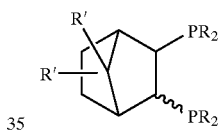

R = cyclohexyl, (C$_6$–C$_{18}$) aryl R' = H, polymer linker or molecular weight enlarging polymer

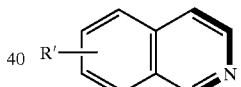

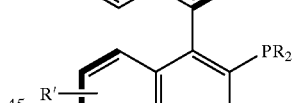

R = cyclohexyl or (C$_6$–C$_{18}$) aryl R' = H, polymer linker or molecular weight enlarging polymer

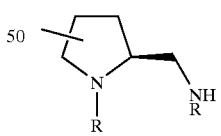

R = H, (C$_1$–C$_8$) alkyl, (C$_7$–C$_{19}$) aralkyl, polymer linker or molecular weight enlarging polymer

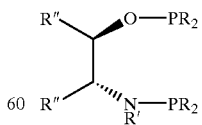

R = cyclohexyl or (C$_6$–C$_{18}$) aryl R' = H, (C$_1$–C$_8$) alkyl, polymer linker or molecular weight enlarging polymer R" H, (C$_1$–C$_8$) alkyl (C$_7$–C$_{19}$) aralkyl, (C$_6$–C$_{18}$) aryl, polymer linker or molecular weight enlarging polymer

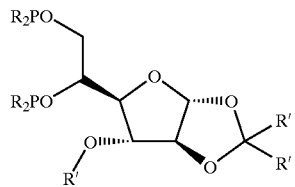

R = cyclohexyl or (C₆–C₁₈) aryl R' = H,
(C₁–C₈) alkyl, (C₇–C₁₉) aralkyl,
(C₆–C₁₈) aryl, polymer linker or molecular weight enlarging polymer

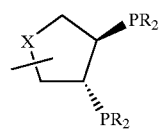

R = cyclohexyl or (C₆–C₁₈) aryl  X = CH₂, O, S, PR or NH

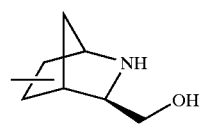

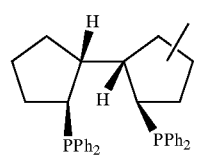

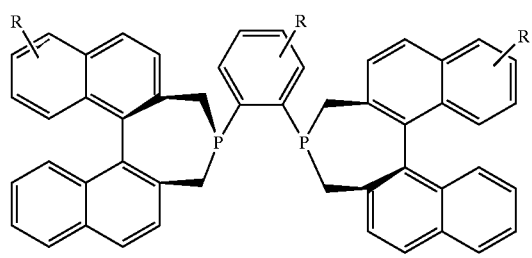

R = H, polymer linker or molecular weight enlarging polymer

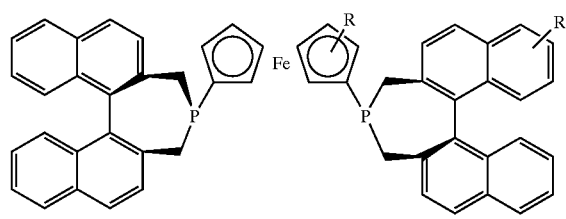

R = H, polymer linker or molecular weight enlarging polymer

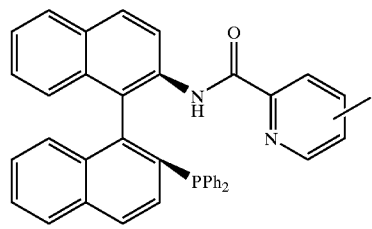

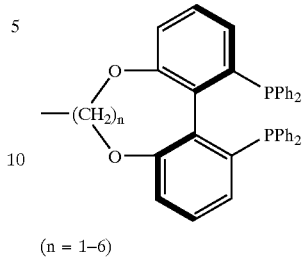

(n = 1–6)

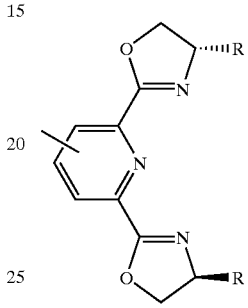

R = (C₁–C₈) alkyl, (C₇–C₁₉) aralkyl,
(C₆–C₁₈) aryl, polymer linker or molecular weight enlarging polymer

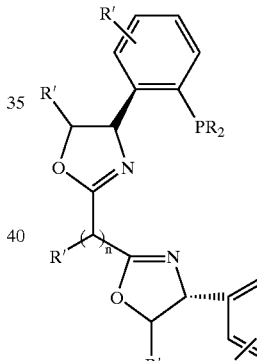

R = cyclohexyl, (C₆–C₁₈) aryl R' H,
(C₁–C₈) alkyl, (C₇–C₁₉) aralkyl,
(C₆–C₁₈) aryl, polymer linker or molecular weight enlarging polymer n = 0–5

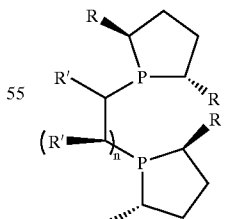

n = 0 or 1  R = (C₁–C₈) alkyl or H
R' = H, (C₁–C₈) alkyl, (C₇–C₁₉) aralkyl,
(C₆–C₁₈) aryl, polymer linker or molecular weight enlarging polymer -continued

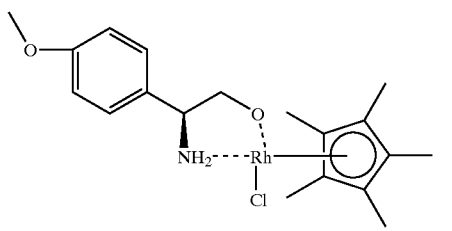

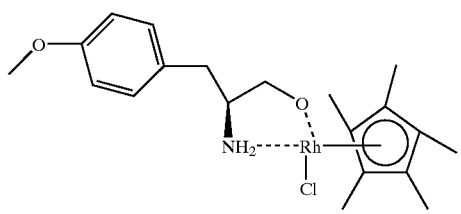

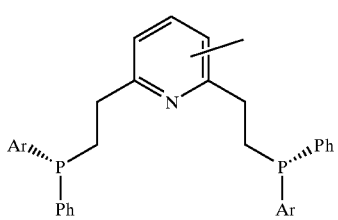

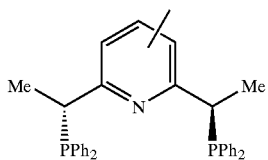

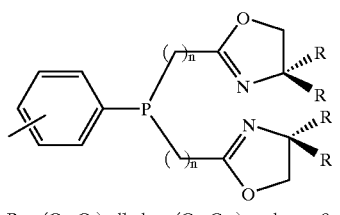

R = (C$_1$–C$_8$) alkyl or (C$_6$–C$_{18}$) aryl, n = 0–5

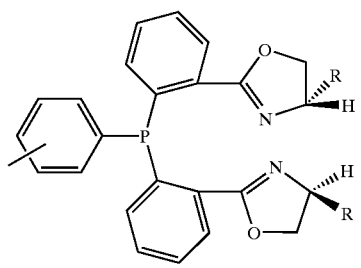

R = (C$_1$–C$_8$) alkyl, (C$_7$–C$_{19}$) aralkyl or (C$_6$–C$_{18}$) aryl

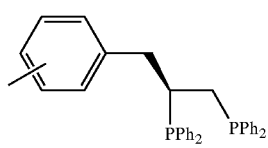

-continued

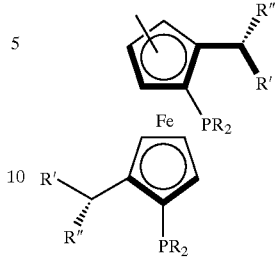

R = cyclohexyl or (C$_6$–C$_{18}$) aryl R' = (C$_1$–C$_8$) alkyl, (C$_6$–C$_{18}$) aryl, polymer linker or molecular weight enlarging polymer R'' = H, (C$_1$–C$_8$) alkyl, (C$_7$–C$_{19}$) aralkyl, (C$_6$–C$_{18}$) aryl, polymer linker or molecular weight enlarging polymer OR', OAc, NR'$_2$ or NH$_2$

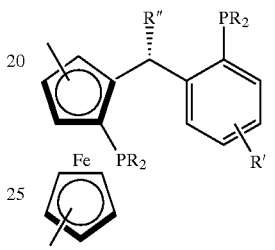

R = cyclohexyl or (C$_6$–C$_{18}$) aryl R' = (C$_1$–C$_8$) alkyl, (C$_6$–C$_{18}$) aryl polymer linker or molecular weight enlarging polymer R'' = H, (C$_1$–C$_8$) alkyl, (C$_6$–C$_{18}$) aryl, OR'', OAc, NR'$_2$, NH$_2$, polymer linker or molecular weight enlarging polymer

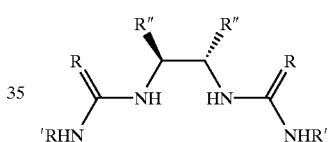

R = O, S, NH R' = H, (C$_1$–C$_8$) alkyl, (C$_7$–C$_{19}$) aralkyl or (C$_6$–C$_{18}$) aryl, polymer linker or molecular weight enlarging polymer R'' = (C$_1$–C$_8$) alkyl, (C$_7$–C$_{19}$) aralkyl, (C$_6$–C$_{18}$) aryl

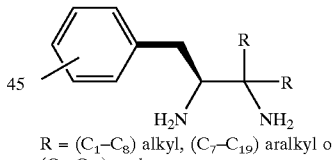

R = (C$_1$–C$_8$) alkyl, (C$_7$–C$_{19}$) aralkyl or (C$_6$–C$_{18}$) aryl

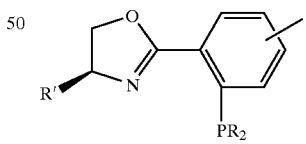

R = (C$_1$–C$_8$) alkyl, (C$_7$–C$_{19}$) aralkyl or (C$_6$–C$_{18}$) aryl R'' = (C$_1$–C$_8$) alkyl, (C$_7$–C$_{19}$) aralkyl or (C$_6$–C$_{18}$) aryl

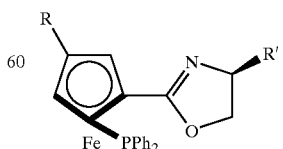

R = polymer linker or molecular weight enlarging polymer or H
R' = (C$_1$–C$_8$) alkyl, (C$_7$–C$_{19}$) aralkyl, (C$_6$–C$_{18}$) aryl polymer linker or molecular weight enlarging polymer

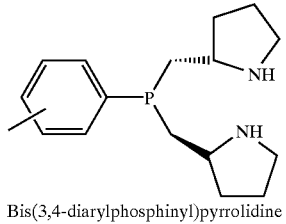

Bis(3,4-diarylphosphinyl)pyrrolidine wherein a line extending from said formulas of said active center represents a bond of a binding site both for the molecular weight enlarging polymer or for the optional polymer linker;

wherein said polymer linker is a member selected from the group consisting of formulae a)–g):

| | | |
|---|---|---|
| a) | —Si(R$_2$)— | |
| b) | —(SiR$_2$—O)$_n$— | n = 1–10000; |
| c) | —(CHR—CHR—O)$_n$— | n = 1–10000; |
| d) | —(X)$_n$— | n = 1–20; |
| e) | Z—(X)$_n$— | n = 0–20; |
| f) | —(X)$_n$—W | n = 0–20; and |
| g) | Z—(X)$_n$—W | n = 0–20; | wherein
R is H, (C$_1$–C$_8$) alkyl, (C$_6$–C$_{18}$) aryl, (C$_7$–C$_{19}$) aralkyl, or ((C$_1$–C$_8$) alkyl)$_{1-3}$-(C$_6$–C$_{18}$) aryl;
X is (C$_6$–C$_{18}$) arylene, (C$_1$–C$_8$) alkylene, (C$_1$–C$_8$) alkenylene, ((C$_1$–C$_8$) alkyl)$_{1-3}$-(C$_6$–C$_{18}$) arylene, or (C$_7$–C$_{19}$) aralkylene;
Z is C(=O)O—, C(=O)NH—, C(=O)—, NR, O, CHR, CH$_2$, C=S, S, PR, Z being bound directly to said molecular weight enlarging polymer; and
W is C(=O)O—, C(=O)NH—, C(=O)—, NR, O, CHR, CH$_2$, C=S, S, PR, W being bound directly to said active center;
wherein the molecular weight-enlarging polymer is a member selected from the group consisting of polyacrylates, polyvinylpyrrolidinones polysiloxanes, polybutadienes, polyisoprenes, polyalkanes, polystyrenes, polyoxazolines and mixtures thereof.

11. The method according to claim 10, wherein said ligand is homogeneously soluble.

12. The method according to claim 10, wherein said homochiral active center is a ligand on a metal or metal ion selected from the group consisting of Ru, Rh, Ir, Pd, Ni, Pt, Co, and ions thereof.

13. The method according to claim 10, wherein said homochiral active center is a catalytically active center.

14. The method according to claim 10, wherein said catalyst further comprises one or more metals or metal ions selected from the group consisting of Ru, Rh, Ir, Pd, Ni, Pt, Co, ions thereof, and mixtures thereof.

15. The method according to claim 10, wherein the reaction is performed in a membrane reactor.

16. The method according to claim 10, wherein the reaction comprises hydrogenating one or more C=C, C=N or C=O double bonds in said starting material.

17. The method according to claim 10, wherein said hydrogenating is performed by transfer hydrogenation.

18. The method according to claim 10, wherein said active center is bound to said polymer linker or said molecular weight-enlarging polymer with one or more of the bonds or polymer linkages in the compounds in said table.

* * * * *